(12) United States Patent
Schall et al.

(10) Patent No.: US 6,992,084 B2
(45) Date of Patent: Jan. 31, 2006

(54) COMPOUNDS AND METHODS FOR MODULATING CXCR3 FUNCTION

(75) Inventors: Thomas J. Schall, San Carlos, CA (US); Daniel J. Dairaghi, Palo Alto, CA (US); Brian E. McMaster, Mountain View, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 47 days.

(21) Appl. No.: 10/279,353

(22) Filed: Oct. 23, 2002

(65) Prior Publication Data

US 2003/0119854 A1    Jun. 26, 2003

Related U.S. Application Data

(63) Continuation of application No. 09/648,329, filed on Aug. 25, 2000, now Pat. No. 6,559,160.

(60) Provisional application No. 60/151,212, filed on Aug. 27, 1999.

(51) Int. Cl.
| | |
|---|---|
| C07D 401/12 | (2006.01) |
| C07D 401/14 | (2006.01) |
| A61K 31/472 | (2006.01) |
| A61K 31/4725 | (2006.01) |
| A61P 11/06 | (2006.01) |

(52) U.S. Cl. .................. 514/235.2; 544/128; 544/287; 544/290; 546/141; 514/309; 514/266.21

(58) Field of Classification Search ................ 546/141; 514/309, 235.2; 544/128
See application file for complete search history.

(56) References Cited

U.S. PATENT DOCUMENTS

| | | | |
|---|---|---|---|
| 5,919,776 A | 7/1999 | Hagmann et al. | |
| 5,948,775 A | 9/1999 | Koko et al. | |

FOREIGN PATENT DOCUMENTS

| | | |
|---|---|---|
| WO | WO 98/02151 A2 | 1/1998 |
| WO | WO 00/00491 A1 | 1/2000 |
| WO | WO 01/30768 A1 | 5/2001 |
| WO | WO 01/31335 A2 | 5/2001 |
| WO | WO 01/98278 A1 | 12/2001 |

OTHER PUBLICATIONS

Power et al. (Current Opinion in Pharmacology, vol. 1, issue 4, Aug. 1, 2001, pp. 417-424).*
Schall, *Cytokine*, 3:165-183 (1991).
Schall et al., *Curr. Opin. Immunol.*, 6:865-873 (1994).
Horuk, *Trends Pharm. Sci.* 15:159-165 (1994).
J.K. Padia et al., "Design and Synthesis of Novel Nonpeptide CCK-B Receptor Antagonists", *Biorganic & Medicinal Chemistry Letters* 7:(7) pp 805-810 (1997).

Thomas J. Schall, Biology of the Rantes/SIS Cytokine Family, *Cytokine, US Academic Press Ltd.*, :3(3),pp 165-183, XP002062534 (May 1, 1991).
Padia et al., Novel Nonpeptide CCK-B Antagonist: Design and Development of Quinazolinone Derivatives as Potent, Selective, and Orally Active CCK-B Antagonists, *Journal of Medical Chemistry*, 41:(7), pp1042-1049 XP002158593 (Mar. 26, 1998).

(Continued)

*Primary Examiner*—Mark L. Berch
*Assistant Examiner*—Kahsay Habte
(74) *Attorney, Agent, or Firm*—Brinks Hofer Gilson & Lione

(57) ABSTRACT

The invention provides compounds and compositions of the formula:

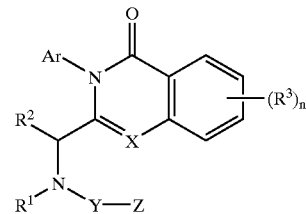

wherein,
the subscript n is an integer of from 0 to 4;
Ar is a member selected from the group consisting of substituted or unsubstituted aryl and substituted or unsubstituted heteroaryl,
$R^1$ is a member selected from the group consisting of substituted or unsubstituted $(C_5-C_{15})$alkyl and $(C_8-C_{14})$acyl group;
$R^2$ is a member selected from the group consisting of substituted or unsubstituted $(C_1-C_8)$alkyl;
each $R^3$ is independently a substituent
Y is a member selected from the group consisting of substituted or unsubstituted $(C_2-C_8)$alkylene and substituted or unsubstituted $(C_2-C_8)$heteroalkylene;
Z is —$NR^4R^5$
$R^4$ and $R^5$ are independently selected from the group consisting of hydrogen and $(C_1-C_8)$alkyl or taken together with the nitrogen atom to which each is attached to form a heterocyclyl or heteroaryl;

These compounds and compositions bind to the CXCR3 chemokine receptor and are useful for treating diseases and conditions responsive to the modulation of CXCR3 activity, such as multiple sclerosis, rheumatoid arthritis, psoriasis, cancer, infectious disease, angiogenesis, and graft rejection.

22 Claims, No Drawings

OTHER PUBLICATIONS

Two pages of ComGenex Compound Catalog (online).

Michael T. Liu et al.; Neutralization of the Chemokine CXCL10 Reduces Inflammatory Cell Invasion and Demyelination and Improves Neurological Function in a Viral Model of Multiple Sclerosis, The American Assoc of Immunology, pp. 4091-4097, 2001.

Torben L. Sorensen et al.; Expression of specific chemokines and chemokine receptors in the central nervous system of multiple sclerosis patients; Journal of Clinical Investigation Mar. 1999 vol. 103 No. 6, pp 807-815.

Konstantin E. Balashov et al.; CCR5$^+$ and CXCR3$^+$ T cells are increased in multiple sclerosis and their ligands MIP-1$\alpha$ and IP-10 are expressed in demyelinating brain lesions; Communicated by Dvid W. Talmage, Proc. Natl. Acad. Sci. USA, vol. 96, pp 6873-6878, Jun. 1999 Immunology.

Craig Gerard and Barrett J. Rollins; Chemokines and disease; Nature Immunology, vol. 2 No. 2 Feb. 2001m http:/Immunol.nature.com, pp108-115.

James B. Rottman et al.; Potential Role of the Chemokine Receptors CXCR3, CCR4, and the Integrin $\alpha E\beta 7$ in the Pathogenesis of Psoriasis Vulgaris; Laboratory Investigation Mar. 2001 vol. 81, No. 3, pp. 335-347.

Carlo Agostini et al., CXC Chemokines IP-10 and Mig Expression and Direct Migration of Pulmonary and Direct Migration of Pulmonary CD8+/CXCR3+ T Cells in the Lungs of Patients with HIV Infection and T-Cell Alveolitis; Am J Respir Crit Med vol. 162, pp1466-1473, 2000.

Wayne W. Hancock et al., Requirement of the Chemokine Receptor CXCR3 for Acute Allograft Rejection; J. Exp. Med. © The Rockefelle University Press vol. 192, No. 10, Nov. 20, 2000, pp. 1515-1519.

Press Release Dec. 10, 2003; Tularik Initiates Phase 2 Clinical Trial of T487 in Psoriasis; San Francisco, CA, pp. 1-2.

* cited by examiner

COMPOUNDS AND METHODS FOR MODULATING CXCR3 FUNCTION

CROSS-REFERENCES TO RELATED APPLICATIONS

This application claims priority of U.S. patent application Ser. No. 09/648,329, filed Aug. 25, 2000, now U.S. Pat. No. 6,559,160 which claimed priority of U.S. Provisional Application Ser. No. 60/151,212, filed Aug. 27, 1999, the disclosures of each of which are incorporated herein by reference in their entireties.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165–183 (1991), Schall, et al., *Curr. Opin. Immunol.*, 6:865–873 (1994) and Murphy, *Rev. Immun.*, 12:593–633 (1994)). In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are four classes of chemokines, CXC ($\alpha$), CC ($\beta$), C($\gamma$), and CX$_3$C ($\delta$), depending on whether the first two cysteines are separated by a single amino acid (C-X-C), are adjacent (C—C), have a missing cysteine pair (C), or are separated by three amino acids (CXC$_3$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381:661–666 (1996)). The C chemokine lymphotactin shows specificity for lymphocytes (Kelner, et al., *Science*, 266:1395–1399 (1994)) while the CX$_3$C chemokine fractalkine shows specificity for lymphocytes and monocytes (Bazan, et al., *Nature*, 385:640–644 (1997).

The chemokines bind specific cell-surface receptors belonging to the family of G-protein-coupled seven-transmembrane-domain proteins (reviewed in Horuk, *Trends Pharm. Sci.*, 15:159–165 (1994)) which are termed "chemokine receptors." On binding their cognate ligands, chemokine receptors transduce an intracellular signal though the associated trimeric G protein, resulting in a rapid increase in intracellular calcium concentration. There are at least twelve human chemokine receptors that bind or respond to β-chemokines with the following characteristic pattern: CCR1 (or "CKR-1" or "CC-CKR-1") MIP-1α, MIP-1β, MCP-3, RANTES (Ben-Barruch, et al., *J. Biol. Chem.*, 270:22123–22128 (1995); Neote, et al., *Cell*, 72:415–425 (1993)); CCR2A and CCR2B (or "CKR-2A"/ "CKR-2A" or "CC-CKR-2A"/"CC-CKR2A") MCP-1, MCP-3, MCP-4; CCR3 (or "CKR-3" or "CC-CKR-3") eotaxin, RANTES, MCP; (Ponath, et al., *J. Exp. Med.*, 183:2437–2448 (1996)); CCR4 (or "CKR-4" or "CC-CKR-4") TARC, MDC (Imai, et al., *J. Biol. Chem.*, 273:1764–1768 (1998)); CCR5 (or "CKR-5" or "CC-CKR-5") MIP-1α, RANTES, MIP-1β (Sanson, et al., *Biochemistry*, 35:3362–3367 (1996)); CCR6 MIP-3 alpha (Greaves, et al., *J. Exp. Med.*, 186:837–844 (1997)); CCR7 MIP-3 beta and 6Ckine (Campbell, et al., *J. Cell. Biol*, 141:1053–1059 (1998)); CCR8 I-309, HHV8 vMIP-I, HHV-8 vMIP-II, MCV vMCC-I (Dairaghi, et al., *J. Biol. Chem.*, 274:21569–21574 (1999)); CCR9 Teck (Zaballos, et al., *J. Immunol.*, 162:5671–5675 (1999)), D6 MIP-1 beta, RANTES, and MCP-3 (Nibbs, et al., *J. Biol. Chem.*, 272: 32078–32083 (1997)), and the Duffy blood-group antigen RANTES, MCP-1 (Chaudhun, et al., *J. Biol. Chem.*, 269: 7835–7838 (1994)).

Chemokine receptors, such as CCR1, CCR2, CCR2A, CCR2B, CCR3, CCR4, CCR5, CCR6, CCR7, CCR8, CCR9, CXCR1, CXCR2, CXCR3, CXCR4, CXCR5, CX$_3$CR1, and XCR1 have been implicated as being important mediators of inflammatory and immunoregulatory disorders and diseases, including asthma and allergic diseases, as well as autoimmune pathologies such as rheumatoid arthritis and atherosclerosis.

The CXCR3 chemokine receptor is expressed primarily in T lymphocytes, and its functional activity can be measured by cytosolic calcium elevation or chemotaxis. The receptor was previously referred to as GPR9 or CKR-L2. Its chromosomal location is unusual among the chemokine receptors in being localized to Xq13. Ligands that have been identified that are selective and of high affinity are the CXC chemokines, IP10, MIG and ITAC.

The highly selective expression of CXCR3 makes it an ideal target for intervention to interrupt inappropriate T cell trafficking. The clinical indications for such intervention are in T-cell mediated autoimmune diseases such as multiple sclerosis, rheumatoid arthritis, and type I diabetes. Inappropriate T-cell infiltration also occurs in psoriasis and other pathogenic skin inflammation conditions, although the diseases may not be true autoimmune disorders. In this regard, up-regulation of IP-10 expression in keratinocytes is a common feature in cutaneous immunopathologies. Inhibition of CXCR3 can be beneficial in reducing rejection in organ transplantation. Ectopic expression of CXCR3 in certain tumors, especially subsets of B cell malignancies indicate that selective inhibitors of CXCR3 will have value in tumor immunotherapy, particularly attenuation of metastasis.

In view of the clinical importance of CXCR3, the identification of compounds that modulate CXCR3 function represent an attractive avenue into the development of new therapeutic agents. Such compounds are the provided herein.

SUMMARY OF THE INVENTION

The present invention is directed to compounds which are modulators of CXCR3 chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of diseases in which CXCR3 chemokine receptors are involved.

More particularly, the compounds provided herein have the general formula:

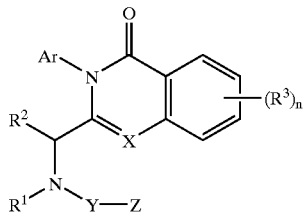

(I)

in which Ar represents a substituted or unsubstituted aryl or heteroaryl group; the symbol $R^1$ represents a substituted or unsubstituted ($C_5$–$C_{15}$)alkyl group; the symbol $R^2$ represents a substituted or unsubstituted ($C_1$–$C_8$)alkyl group; the subscript n is an integer of from 0 to 4, and each $R^3$ independently represents an aryl substituent, preferably selected from halogen, hydroxy, ($C_1$–$C_8$)alkyl, ($C_1$–$C_8$) alkoxy, nitro, cyano, amino, and mono- or di-alkylamino; X is CH or N; Y is a substituted or unsubstituted ($C_2$–$C_8$) alkylene or ($C_2$–$C_8$)heteroalkylene; and Z is —$NR^4R^5$, in which $R^4$ and $R^5$ are independently hydrogen or ($C_1$–$C_8$) alkyl.

DESCRIPTION OF THE INVENTION

Abbreviations and Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR'—C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted (C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro (C$_1$–C$_4$)alkoxy, and perfluoro (C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl)oxy-(C$_1$–C$_4$)alkyl.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

The present invention is directed to compounds, compositions and methods useful in the modulation of chemokine receptor activity, particularly CXCR3. Accordingly, the compounds of the present invention are those which inhibit at least one function or characteristic of a mammalian CXCR3 protein, for example, a human CXCR3 protein. The ability of a compound to inhibit such a function can be demonstrated in a binding assay (e.g., ligand binding or promotor binding), a signalling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes).

Compounds that Modulate CXCR3 Activity

In one aspect, the present invention provides compounds that modulate CXCR3 activity. The compounds have the general formula:

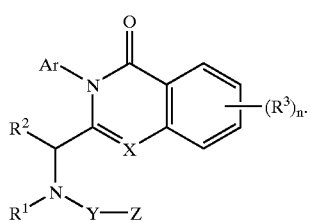

(I)

In the formula I, the symbol Ar represents a substituted or unsubstituted aryl or heteroaryl group. Preferably, Ar is a substituted or unsubstituted aryl group, more preferably a substituted aryl group. In one group of particularly preferred embodiments, Ar represents a substituted phenyl group. Preferred substituents on the phenyl group are selected from halogen, ($C_1$–$C_4$)alkyl, ($C_1$–$C_4$)haloalkyl, ($C_1$–$C_4$)alkoxy, ($C_1$–$C_4$)haloalkoxy, nitro and cyano. More preferably, the substituents on the phenyl group are selected from halogen and ($C_1$–$C_4$)alkoxy.

Returning to formula I above, the symbol $R^1$ represents a substituted or unsubstituted ($C_5$–$C_{15}$)alkyl group, preferably, a substituted ($C_5$–$C_{15}$)alkyl group. In a particularly preferred group of embodiments, $R^1$ is a ($C_5$–$C_{15}$)acyl group which is either saturated or unsaturated. Examples of preferred $R^1$ groups include pentanoyl, hexanoyl, hetanoyl, octanoyl, decanoyl and the like. Most preferably, $R^1$ is a ($C_8$–$C_{14}$)acyl group.

The symbol $R^2$ represents a substituted or unsubstituted ($C_1$–$C_8$)alkyl group. Preferably, $R^2$ is an unsubstituted ($C_1$–$C_8$)alkyl group, more preferably an unsubstituted ($C_1$–$C_4$)alkyl group. In further preferred embodiments, $R^2$ is a methyl, ethyl or propyl group, most preferably a methyl group.

The symbol —($R^3$)$_n$ represents a variety of aryl group substituents which can occupy any of the available valences on the aromatic ring. For those embodiments in which n is an integer of from 2 to 4 (multiple substitution), each of the $R^3$ groups will be independently selected from the available list (see the definition section relating to substituents for an aryl or heteroaryl group). Preferably, each $R^3$ is independently a halogen, hydroxy, ($C_1$–$C_8$)alkyl, ($C_1$–$C_8$)alkoxy, nitro, cyano, amino, and mono- or di-alkylamino. In preferred embodiments, n is an integer from 0 to 2, and each $R^3$ (when present) is selected from halogen, hydroxy, ($C_1$–$C_4$) alkyl, ($C_1$–$C_4$)alkoxy, and nitro.

In formula I above, the letter X represents CH or N, preferably N.

The letter Y represents a linking group which can be a substituted or unsubstituted ($C_2$–$C_8$)alkylene or ($C_2$–$C_8$) heteroalkylene linking group. Exemplary of such linking groups are —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$CH$_2$—, —CH$_2$CH$_2$OCH$_2$CH$_2$—, and the like.

The letter Z represents —NR$^4$R$^5$, in which R$^4$ and R$^5$ are independently hydrogen or ($C_1$–$C_8$)alkyl, or R$^4$ and R$^5$ can be combined with the nitrogen to which each is attached to form a five-, six-, or seven membered ring. Preferably, R$^4$ and R$^5$ are the same and are selected from methyl, ethyl and propyl, or are combined with the nitrogen to which each is attached to form a pyrrolidine ring. In a particularly preferred group of embodiments Z is a dimethyl amino group.

In addition to the preferred embodiments provided for each of the substituents above, certain combinations of substituents are also preferred within the present invention. For example, in one group of preferred embodiments, X is N, Ar is substituted phenyl and R$^1$ is a (C$_8$–C$_{14}$)acyl group. More preferably, X is N, Ar is substituted phenyl, R$^1$ is a (C$_8$–C$_{14}$)acyl group and R$^2$ is unsubstituted (C$_1$–C$_4$)alkyl. Still more preferably, X is N, Ar is substituted phenyl, R$^1$ is a (C$_8$–C$_{14}$)acyl group, R$^2$ is unsubstituted (C$_1$–C$_4$)alkyl and Y is (C$_2$–C$_5$)alkylene. In still further preferred embodiments, X is N, Ar is substituted phenyl, R$^1$ is a (C$_8$–C$_{14}$)acyl group, R$^2$ is unsubstituted (C$_1$–C$_4$)alkyl, Y is (C$_2$–C$_5$)alkylene and Z is dimethylamino.

In yet another group of preferred embodiments, n is 0, X is N, Ar is substituted phenyl, R$^1$ is a (C$_8$–C$_{14}$)acyl group, R$^2$ is unsubstituted (C$_1$–C$_4$)alkyl, Y is ethylene and Z is dimethylamino. Most preferably, n is 0, X is N, R$^1$ is a (C$_8$–C$_{14}$) acyl group, R$^2$ is unsubstituted (C$_1$–C$_4$)alkyl, Y is ethylene, Z is dimethylamino and Ar is a 4-substituted phenyl group, more preferably, 4-fluorophenyl, 4-chlorophenyl, 4-bromophenyl, 4-methylphenyl, and 4-methoxyphenyl.

In a group of most preferred embodiments, the compound has a formula selected from the group:

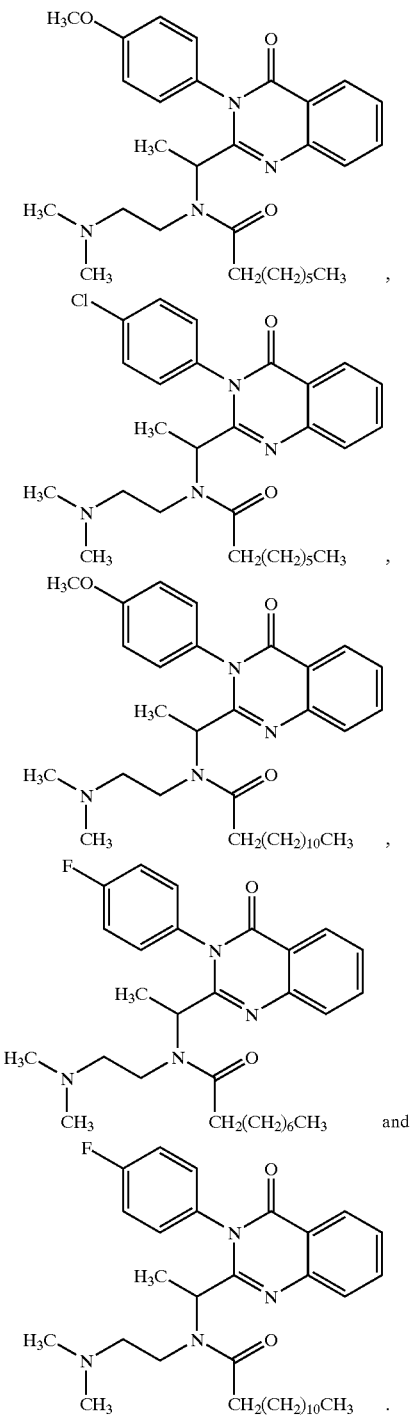

Compositions that Modulate CXCR3 Activity

In another aspect, the present invention provides compositions for modulating chemokine receptor activity in humans and animals. The compositions comprise a compound of the present invention with a pharmaceutical carrier or diluent.

"Modulation" of chemokine receptor activity, as used herein in its various forms, is intended to encompass antagonism, agonism, partial antagonism and/or partial agonism of the activity associated with a particular chemokine receptor, preferably the CXCR3 receptor. The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically active compounds as noted herein which are usually applied in the treatment of the above mentioned pathological conditions.

Methods of Treating CXCR3-Mediated Conditions or Diseases

In yet another aspect, the present invention provides methods of treating CXCR3-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated with the present compounds and compositions. In one group of embodiments, diseases or conditions, including chronic diseases, of humans or other species can be treated with inhibitors of CXCR3 function. These diseases or conditions include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), multiple sclerosis, systemic lupus erythematosus, diabetes, glomerulonephritis, and the like, (3) graft rejection (including allograft rejection and graft-v-host disease), and (4) other diseases in which undesired inflammatory responses are to be inhibited (e.g., atherosclerosis, myositis, neurodegenerative diseases, Alzheimer's disease, encephalitis, meningitis, hepatitis, nephritis, sepsis, sarcoidosis, conjunctivitis, otitis, chronic obstructive pulmonary disease, sinusitis and Behcet's syndrome). In another group of embodiments, diseases or conditions are treated with agonists of CXCR3 function. Examples of diseases to be treated with CXCR3 agonists include cancers, diseases in which angiogenesis or neovascularization play a role (neoplastic diseases, retinopathy and macular degeneration), infectious diseases and immunosuppressive diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat inflammatory and immunoregulatory disorders and diseases, including asthma and allergic diseases, as well as autoimmune pathologies such as rheumatoid arthritis and atherosclerosis, and those pathologies noted above.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as .beta.2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), .alpha.-glucosidase inhibitors (acarbose) and glitazones (troglitazone and pioglitazone); (l) preparations of interferon beta (interferon beta-1.alpha., interferon beta-1.beta.); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Method of Evaluating Putative CXCR3 Modulators

In yet another aspect, the present invention includes methods to evaluate putative specific agonists or antagonists of CXCR3 function. Accordingly, the present invention is directed to the use of these compounds in the preparation and execution of screening assays for compounds which modulate the activity of the CXCR3 chemokine receptor. For example, the compounds of this invention are useful for isolating receptor mutants, which are excellent screening tools for more potent compounds. Furthermore, the compounds of this invention are useful in establishing or determining the binding site of other compounds to the CXCR3 chemokine receptor, e.g., by competitive inhibition. The compounds of the instant invention are also useful for the evaluation of putative specific modulators of the CXCR3 chemokine receptor, relative to other chemokine receptors including CCR-1, CCR-2, CCR-2A, CCR-2B, CCR-3, CCR-4, CCR-5 and CXCR-4. One of skill in the art will appreciate that thorough evaluation of specific agonists and antagonists of the above chemokine receptors has been hampered by the lack of availability of non-peptidyl (metabolically resistant) compounds with high binding affinity for these receptors. Thus the compounds provided herein are particularly useful in this context.

Preparation of CXCR3 Modulators

The compounds of formula I used in the present invention can be prepared according to general synthesis schemes provided below.

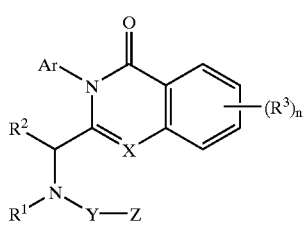

(I)

As shown in Scheme 1, a substituted anthranilic acid (i) can be acylated with an appropriate acid chloride (typically in a solvent such as DMF) to form the amide derivative ii. Cyclization of ii with, for example, acetic anhydride forms a benzoxazinone iii. Introduction of an aryl side group can be accomplished by treating iii with an aniline derivative or a heteroaryl amine to effect formation of the quinazolin-4-one ring and produce iv. Further manipulations of the appendage in the C2 position of the quinazolin-4-one ring can be carried out by first brominating the carbon attached to C2 for form v, and then displacing the bromine leaving group with, for example $Z-Y-NH_2$ to form vi. Examples of suitable nucleophiles include N,N-dimethylethylenediammine, N,N-dimethylpropylenediammine and the like.

Finally, alkylation (or acylation) of the amino group with $R^1$—X provides the title compound vii.

Several points in the synthetic route allow for functional group replacement. Substituted anthranilic acids (i, Scheme 1) can be used to introduce/modify the substitution of the 3H-quinazolin-4-one 5–8 positions (e.g. $R^3$ of formula I). Modification of the 2-alkyl group (e.g. $R^2$ of formula I) can be accomplished by introducing a variety of acyl groups in the first step (cf. step a, Scheme 1). Likewise the 3N-phenyl group (e.g. Ar) is varied by selecting from a large number of substituted anilines to use in the 3H-quinazolin-4-one forming third step of Scheme 1. Finally, the alkyl amino functionality (e.g. $R^1$, Y, and Z) is modified in the fifth and sixth steps. The route is most amenable to the rapid generation of analogs differing in the alkyl amino functionality (e.g. $R^1$, Y, and Z) because these groups are introduced in the final two steps.

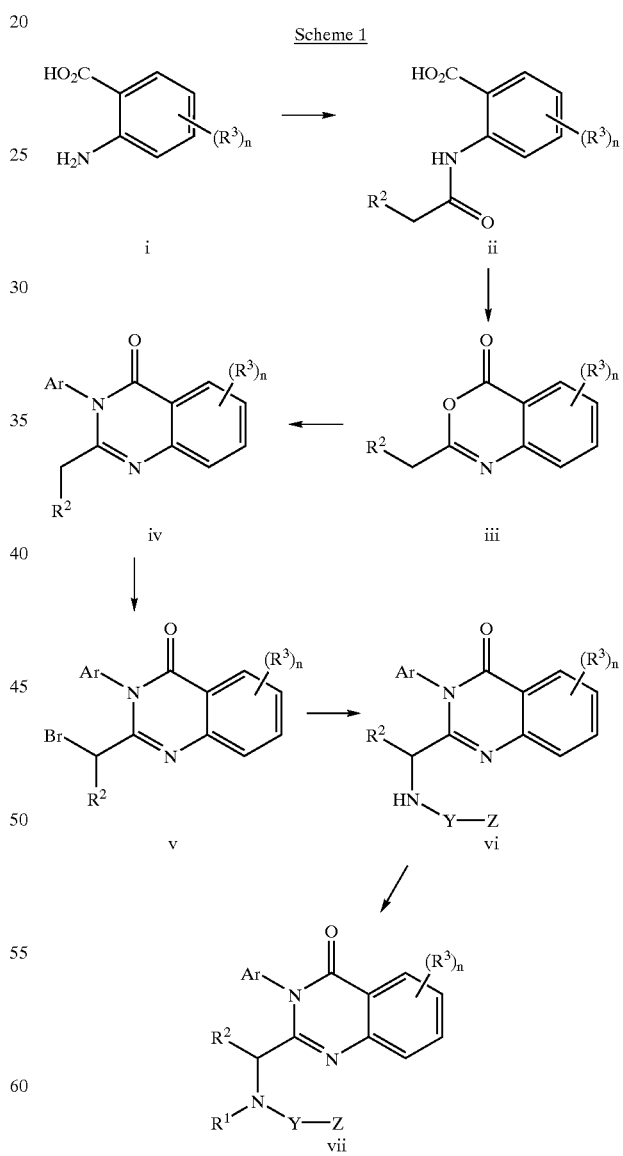

A second method for the synthesis of 3H-quinazolin-4-ones decreases the number of steps and facilitates modification of the quinazolinone core (e.g. $R^3$ and Ar in formula I). In Scheme 2, the 3H-quinazolino-4-one core is assembled in one step from the acylated anthranilic acid and an aniline (cf. step b, Scheme 2). The fewer steps in this method provided a more convenient route to modify the 3H-quinazolin-4-one substitution (e.g. $R^3$ in formula I, and $R_A$ in Scheme 2). Aside from the single step reaction to generate the 3H-quinazolin-4-one core (cf. step b, Scheme 2), the synthetic sequence of Scheme 2 mimics that of Scheme 1.

Scheme 2

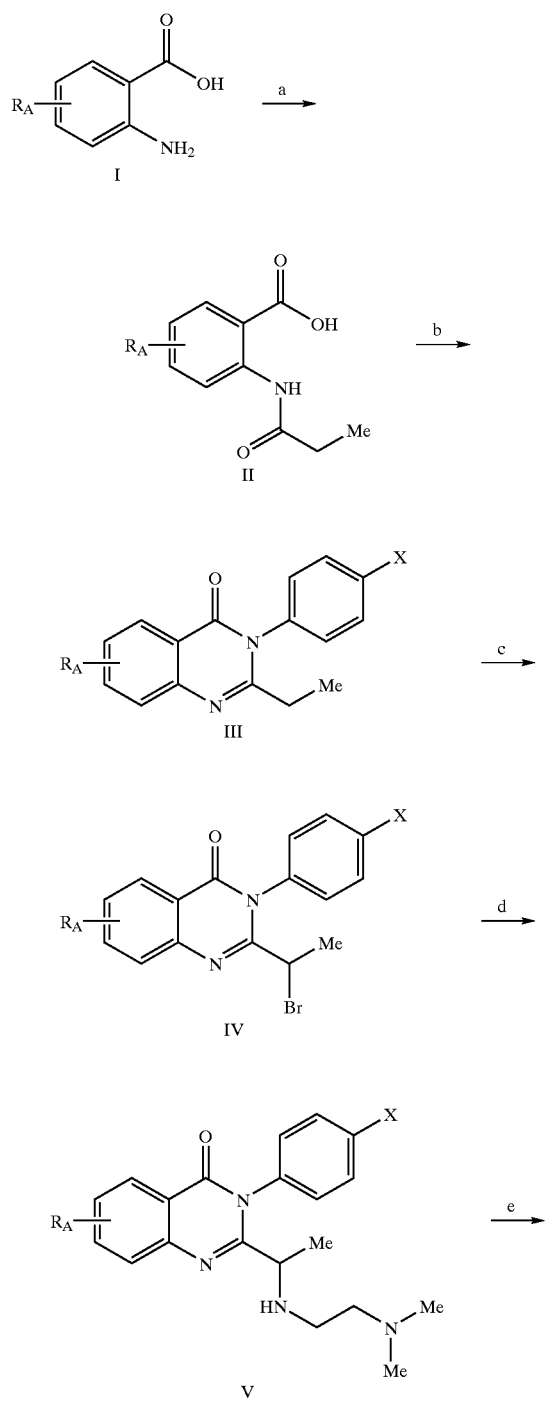

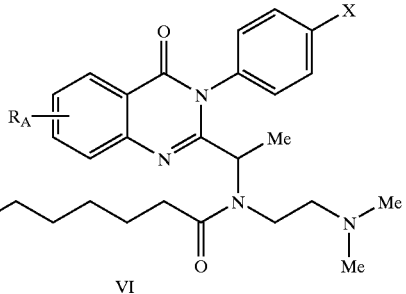

X = F, OMe  $R_A$ = 6-OMe, 6-Cl, 6-$NO_2$
6-Me, 6-I, 5-F, 6,7,8-OMe (a) propionyl chloride, DMF, RT
(b) $PCl_3$, 4-fluoroaniline, toluene, 110° C.
(c) $Br_2$, NaOAc, HOAc, 40° C.
(d) 1-(N,N-dimethylamino)-2-aminoethane, EtOH, 80° C.
(e) decanoyl chloride, $NET_3$, cat. DMAP, 1,4-dioxane Evaluation Assays for CXCR3 Modulators A variety of assays can be used to evaluate the compounds provided herein, including CXCR3 binding assays, CXCR3 signalling assays, chemotaxis assays, and other assays of cellular response.

In a suitable assay, a CXCR3 protein (whether isolated or recombinant) is used which has at least one property, activity or functional characteristic of a mammalian CXCR3 protein. The property can be a binding property (to, for example, a ligand or inhibitor), a signalling activity (e.g., activation of a mammalian G protein, induction of rapid and transient increase in the concentration of cytosolic free calcium $[Ca^{++}]_i$), cellular response function (e.g., stimulation of chemotaxis or inflammatory mediator release by leukocytes), and the like.

In one embodiment, a composition containing a CXCR3 protein or variant thereof is maintained under conditions suitable for binding. The CXCR3 receptor is contacted with a putative agent (or a second composition containing at least one putative agent) to be test, and binding is detected or measured.

In one group of preferred embodiments, the assay is a cell-based assay and cells are used which are stably or transiently transfected with a vector or expression cassette having a nucleic acid sequence which encodes the CXCR3 receptor. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., IP-10, ITAC or Mig) as a competitor.

In other embodiments, binding inhibition assays can be used to evaluate the present compounds. In these assays, the compounds are evaluated as inhibitors of ligand binding using, for example, IP-10, ITAC or Mig. In this embodiment, the CXCR3 receptor is contacted with a ligand such as IP-10, ITAC or Mig and a measure of ligand binding is made. The receptor is then contacted with a test agent in the presence of a ligand (e.g., IP-10 or Mig) and a second measurement of binding is made. A reduction in the extent of ligand binding is indicative of inhibition of binding by the test agent. The binding inhibition assays can be carried out using whole cells which express CXCR3, or a membrane fraction from cells which express CXCR3.

The binding of a G protein-coupled receptor by, for example, an agonist, can result in a signalling event by the receptor. Accordingly, signalling assays can also be used to evaluate the compounds of the present invention and induction of signalling function by an agent can be monitored using any suitable method. For example, G protein activity, such as hydrolysis of GTP to GDP, or later signalling events triggered by receptor binding can be assayed by known methods (see, for example, PCT/US97/15915; Neote, et al., *Cell*, 72:415–425 (1993); Van Riper, et al., *J. Exp. Med.*, 177:851–856 (1993) and Dahinden, et al., *J. Exp. Med.*, 179:751–756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. Suitable assays are described in PCT/US97/15915; Springer, et al., WO 94/20142; Berman et al., *Immunol. Invest.*, 17:625–677 (1988); and Kavanaugh et al., *J. Immunol.*, 146:4149–4156 (1991)).

The compounds provided herein can also be evaluated using models of inflammation to assess the ability of the compound to exert an effect in vivo. Suitable models are described as follows: a sheep model for asthma (see, Weg, et al., *J. Exp. Med.*, 177:561 (1993)); and a rat delayed-type hypersensitivity model (see Rand, et al., *Am. J. Pathol.*, 148:855–864 (1996)). Another useful model for evaluating the instant compounds is the experimental autoimmune encephalomyelitis (EAE) model for multiple sclerosis, which probes chemokine receptor expression and function (see, Ransohoff, et al., *Cytokine Growth Factor Rev.*, 7:35–46 (1996), and Karpus, et al., *J. Immunol.* 161:2667–2671 (1998)).

In addition, leukocyte infiltration assays can also be used to evaluate a compound (see, Van Damme, et al., *J. Exp. Med.*, 176:59–65 (1992); Zachariae, et al., *J. Exp. Med.*, 171:2177–2182 (1990); and Jose, et al., *J. Exp. Med.*, 179:881–887 (1994)).

EXAMPLES

The following examples are offered to illustrate, but not to limit the claimed invention.

In the examples below, unless otherwise stated, temperatures are given in degrees Celsius (°C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

Example 1

This example illustrates a six step synthesis of compound 1.11.

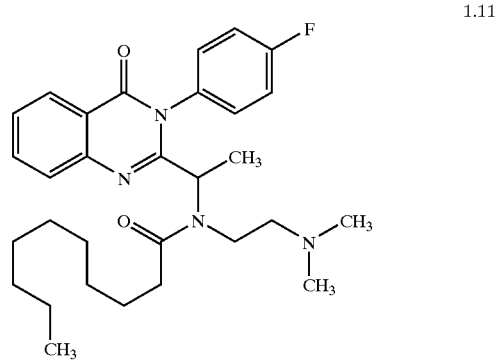

1.1 Amidation of Anthranilic Acid

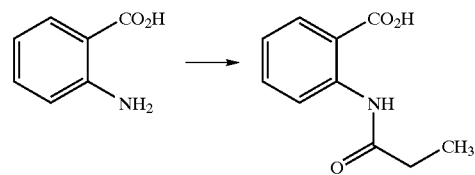

To a three-necked, 500 mL round-bottom flask equipped with thermometer, dropping funnel, and an efficient magnetic stir bar containing anthranilic acid (0.5 mole, 68.5 g) and N,N-dimethylformamide (250 mL) was added propionyl chloride (0.55 mole, 47.8 ml) dropwise at such a rate that the temperature of the mixture remained below 40° C. The product began to precipitate after about one half of the acid chloride was added, and the suspension was stirred vigorously at room temperature for an additional two hours after addition was completed. The resulting mixture was poured into water (2.0 L) and stirred for an additional one hour. The precipitated product was collected by filtration, washed with cold water, and dried in a desiccator at room temperature under reduced pressure over $P_2O_5$ to provide the title compound (62.8 g, 65% yield).

1.2 Cyclization of N-Propionyl Anthranilic Acid (a).

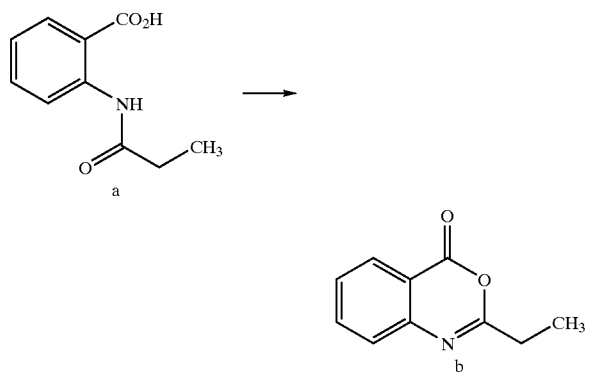

Compound a (48.3 g, 0.25 mole) was dissolved in acetic anhydride (180 mL) in a 500-mL round-bottom flask equipped with magnetic stir bar and Claisen-distillation head (with vacuum inlet). The flask was slowly heated in an oil bath to a bath temperature of 170–180° C. The reaction mixture was stirred vigorously and the acetic acid produced was slowly distilled off under atmospheric pressure. Once the vapor temperature of the distillate reached about 140° C., the reaction mixture was heated for an additional 15 min, then cooled until the temperature reached 60° C. The excess acetic anhydride was removed by distillation under reduced pressure (about 20 mmHg). The residue was cooled and the product solidified. The solid product was triturated with n-hexane (75 mL), and isolated by filtration to provide compound b (31.5 g, 72%) which was carried on without purification.

1.3 Addition of 4-fluoroaniline to 2-ethyl-3,1-[4H]benzoxazine-4-one (b)

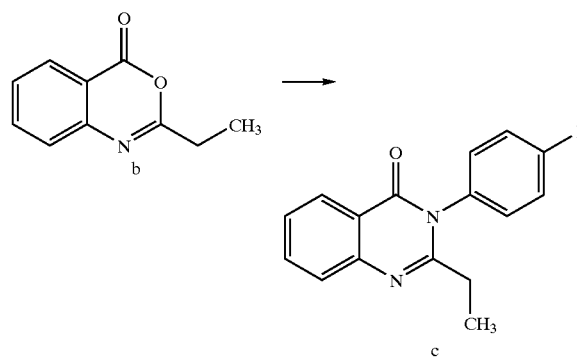

Compound b (31.5 g, 0.18 mole) and 4-fluoroaniline (18.7 g, 0.19 mole) were combined in chloroform (75 mL) and heated to reflux for 9 h. After TLC indicated that the starting material had been consumed, the chloroform was evaporated under reduced pressure. Ethylene glycol (50 mL) and NaOH pellets (0.32 g) were added to the residue and the flask was equipped with a Claisen-distillation head and a magnetic stir bar. The flask was immersed in an oil bath and reheated up to 130–140° C. bath temperature with vigorous stirring and maintained at that temperature for 5 h as water was removed by distillation. After completion of the reaction, the clear solution was cooled to room temperature and left overnight to completely precipitate the product. The pH of the suspension was adjusted to pH 7–8 by adding 3% aq. HCl. The crystalline product was filtered off and washed with cold water then recrystallized from isopropanol to provide compound c (27.0 g, 56% yield).

1.4 Bromination of 2-ethyl-3-(4-fluorophenyl)quinazolin-4-one (c)

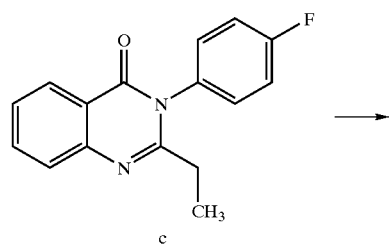

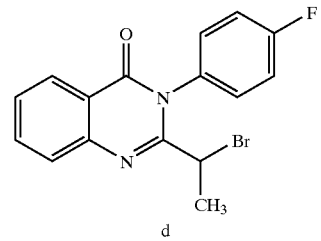

Compound c (26.8 g, 0.10 mole), anhydrous sodium acetate (10.0 g) and glacial acetic acid (130 mL) were combined in a three-necked 250 mL round-bottom flask equipped with thermometer, dropping funnel, and an efficient magnetic stir bar. A solution of bromine (16.0 g, 0,10 mole) in acetic acid (10 mL) was added dropwise to the above solution at 40° C. over a period of about 1–2 h. After addition was completed the mixture was poured into water (1500 mL) and stirred at room temperature for about 1–2 h. The precipitated product was isolated by filtration, washed with warm water to remove the trace of the acetic acid, then rinsed with a small amount of isopropanol and dried to provide (31.2 g, 90 % yield) of compound d.

1.5 Addition of N,N-dimethylethylenediamine to Compound d

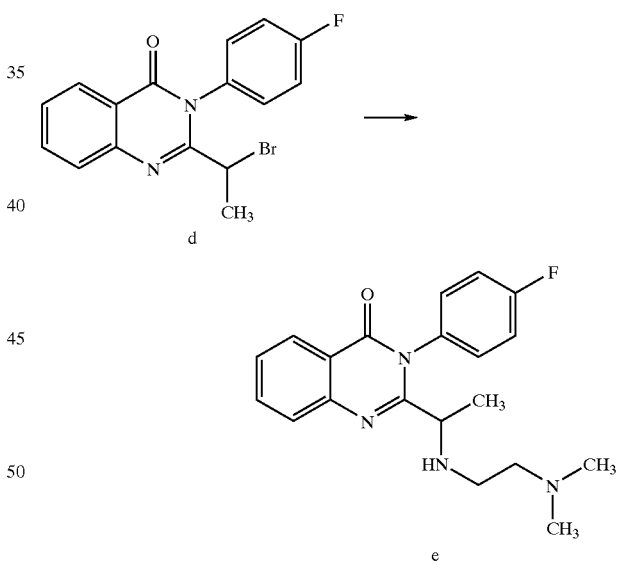

Compound d (6.94 g, 0.020 mole) and N,N-dimethylethylenediamine (3.56 mL, 0.032 mole) were combined in ethanol (30 mL) and heated to reflux for 5 h. After cooling, the solvent was evaporated under reduced pressure. The residue was dissolved in $CH_2Cl_2$ and washed once with 10% aq. $Na_2CO_3$ solution then with water. The organic phase was dried over $MgSO_4$, filtered and evaporated to dryness under reduced pressure. The resulting crude product was purified by column chromatography on silica gel adsorbent with an eluent of $CHCl_3$-MeOH 20:1 to provide compound e (3.2 g, 45% yield).

1.6 Acylation of Compound e

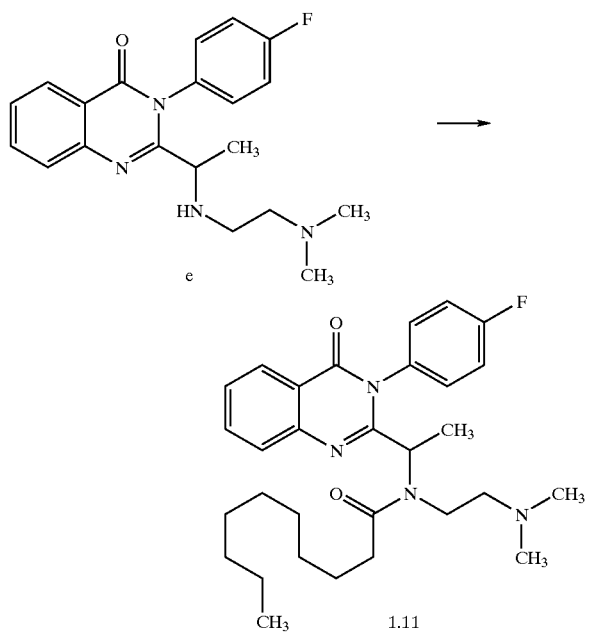

Compound e (354 mg, 1 mmole) was dissolved in a mixture of 1,4-dioxane (3 mL) and triethylamine (0.14 mL, 1 mmol). The reaction mixture was placed in a water bath and decanoyl chloride (0.21 mL, 1 mmole) was added. The resulting mixture was slowly stirred for 15 h at room temperature, then concentrated under reduced pressure. The residue was dissolved in $CH_2Cl_2$ and washed successfully with 10% aq. $Na_2CO_3$ solution then twice with water. The organic phase was dried over $MgSO_4$, filtered and evaporated to dryness under reduced pressure to provide compound 1.11 (3.2 g, 80% yield).

Example 2

This example illustrates the preparation of additional compounds using the methodology described above.

Preparation of Compound 2.1

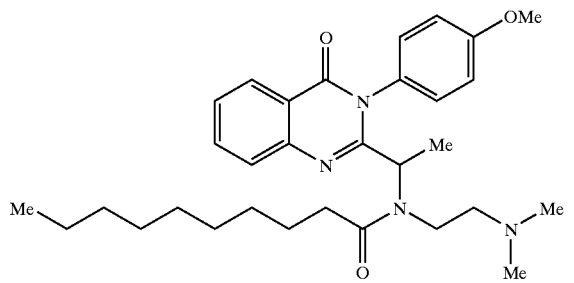

Decanoic acid
(2-dimethylamino-ethyl)-{1-[3-(4-methoxy-phenyl)-4-oxo-3,4-dihydro-quinazolin-2-yl]-ethyl}-amide
(Compound 2.1)

Compound 2.1 was prepared following the methods described above for 1.11, with the exception that 4-methoxyaniline was used in place of 4-fluoroaniline. Characterization data for 2.1 follows: colorless viscous oil; $^1$H NMR ($d_6$-DMSO; T=140° C.) δ 0.90 (t, 3H, J=7.2 Hz), 1.16–1.48 (m, 14H), 1.46 (d, 3H, J=6.8 Hz), 1.92–2.10 (m, 2H), 2.05 (s, 6H), 2.16–2.24 (m, 1H), 2.41 (ddd, 1H, $J_1$=5.2 Hz, $J_2$=8.8 Hz, $J_3$=12.0 Hz), 3.30 (ddd, 1H, $J_1$=4.8 Hz, $J_2$=8.4 Hz, $J_3$=14.0 Hz), 3.41 (ddd, 1H, $J_1$=6.0 Hz, $J_2$=9.2 Hz, $J_3$=14.8 Hz), 3.86 (s, 3H), 5.10 (br q, 1H, J=5.6 Hz), 7.05 (br m, 2H), 7.20 (br m, 1H), 7.32 (br m, 1H), 7.54 (ddd, 1H, $J_1$=1.2 Hz, $J_2$=8.0 Hz, $J_3$=8.2 Hz), 7.72 (d, 1H, J=8.0 Hz), 7.84 (ddd, 1H, $J_1$=2.0 Hz, $J_2$=7.2 Hz, $J_3$=8.4 Hz), 8.15 (dd, $J_1$=0.8 Hz, $J_2$=7.6 Hz) ppm. At room temperature, compound exists as a mixture of cis/trans amide rotamers, ca. 3:2 by $^1$H NMR ($d_6$-DMSO; T=25° C.) δ 4.82 (q, 1.4H, J=6.8 Hz) & 5.19 (q, 1.0H, J=7.2 Hz) ppm. MS (ESI$^+$) 521.5 [MH]$^+$.

Preparation of Compound 2.2

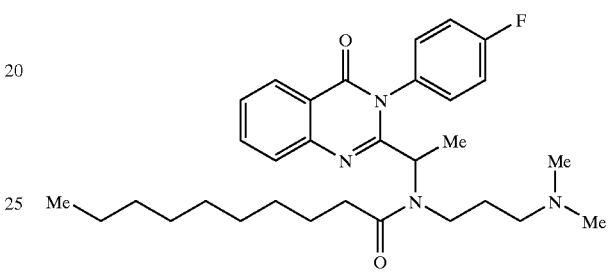

Decanoic acid
(3-dimethylamino-propyl)-{1-[3-(4-fluoro-phenyl)-4-oxo-3,4-dihydro-quinazolin-2-yl]-ethyl}-amide
(Compound 2.2)

Compound 2.2 was prepared following the methods described above for 1.11, with the exception that 3-(dimethylamino)-1-aminopropane was used in place of 2-(dimethylamino)aminoethane. Characterization data for 2.2 follows: colorless viscous oil; $^1$H NMR ($d_6$-DMSO; T=140° C.) δ 0.89 (t, 3H, J=6.8 Hz), 1.20–1.48 (m, 14H), 1.45 (d, 3H, J=6.8 Hz), 1.50–1.74 (m, 2H), 1.98–2.07 (m, 1H), 2.05 (s, 6H), 2.08–2.22 (m, 3H), 3.21 (ddd, 1H, $J_1$=5.6 Hz, $J_2$=10.4 Hz, $J_3$=15.2 Hz), 3.34 (ddd, 1H, $J_1$=5.2 Hz, $J_2$=10.0 Hz, $J_3$=15.2 Hz), 5.13 (q, 1H, J=6.0 Hz), 7.30 (br m, 3H), 7.49 (br m, 1H), 7.55 (ddd, 1H, $J_1$=1.2 Hz, $J_2$=7.2 Hz, $J_3$=8.0 Hz), 7.72 (d, 1H, J=8.0 Hz), 7.85 (ddd, 1H, $J_1$=1.2 Hz, $J_2$=6.8 Hz, $J_3$=8.0 Hz), 8.14 (dd, 1H, $J_1$=1.2 Hz, $J_2$=8.0 Hz) ppm. At room temperature, compound exists as a mixture of cis/trans amide rotamers, ca. 2:3 by $^1$H NMR ($d_6$-DMSO; T=25° C.) δ 4.78 (q, 1.0H, J=6.8 Hz) & 5.24 (q, 1.5H, J=6.8 Hz) ppm. MS (ESI$^+$) 523.4 [MH]$^+$.

Preparation of Compound 2.3

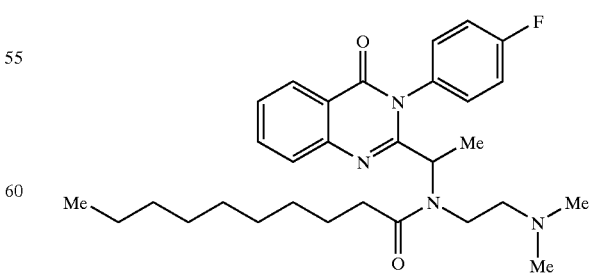

2-{1-[Decyl-(2-dimethylamino-ethyl)-amino]-ethyl}-3-(4-fluoro-phenyl)-3H-quinazolin-4-one
(Compound 2.3)

Compound 2.3 was prepared following the methods described above for 1.11, with the exception that 1-iodo-decane was used in place of decanoyl chloride. Characterization data for 2.3 follows: colorless viscous oil; $^1$H NMR (CDCl$_3$) δ 0.87 (t, 3H, J=7.6 Hz), 1.20–1.35 (m, 15H), 1.66–1.74 (m, 2H), 2.88–2.96 (m, 1H), 3.09–3.16 (m, 1H), 3.40 (s, 6H), 3.47 (q, 1H, J=6.8 Hz), 3.56–3.62 (m, 2H), 3.62–3.71 (m, 1H), 3.73–3.80 (m, 1H), 7.24 (m, 2H), 7.37 (m, 2H), 7.49 (ddd, 1H, J$_1$=1.2 Hz, J$_2$=J$_3$=8.0 Hz), 7.71 (d, 1H, J=7.2 Hz), 7.79 (ddd, 1H, J$_1$=1.6 Hz, J$_2$=6.8 Hz, J$_3$=8.4 Hz), 8.25 (dd, 1H, J$_1$=1.2 Hz, J$_2$=8.0 Hz) ppm. MS (ESI$^+$) 495.4 [MH]$^+$.

Preparation of Compound 2.4

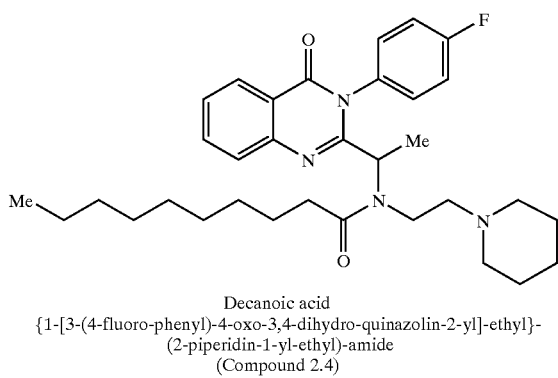

Decanoic acid
{1-[3-(4-fluoro-phenyl)-4-oxo-3,4-dihydro-quinazolin-2-yl]-ethyl}-
(2-piperidin-1-yl-ethyl)-amide
(Compound 2.4)

Compound 2.4 was prepared following the methods described above for 1.11, with the exception that 1-(2-aminoethyl)piperidine was used in place of 2-(dimethy-lamino)-1-aminoethane. Characterization data for 2.4 follows: colorless viscous oil; $^1$H NMR (d$_6$-DMSO; T=140° C.) δ 0.89 (t, 3H, J=6.8 Hz), 1.18–1.48 (m, 20H), 1.45 (d, 3H, J=6.4 Hz), 1.98–2.08 (m, 2H), 2.18–2.33 (m, 5H), 2.40–2.48 (m, 1H), 3.29 (ddd, 1H, J$_1$=5.6 Hz, J$_2$=8.8 Hz, J$_3$=14.4 Hz), 3.43 (ddd, 1H, J$_1$=5.2 Hz, J$_2$=8.4 Hz, J$_3$=14.0 Hz), 5.11 (br m, 1H), 7.30 (br m, 3H), 7.49 (br m, 1H), 7.55 (dd, 1H, J$_1$=7.6 Hz, J$_2$=8.0 Hz), 7.72 (d, 1H, J=7.6 Hz), 7.85 (ddd, 1H, J$_1$=1.2 Hz, J$_2$=7.2 Hz, J$_3$=8.4 Hz), 8.14 (dd, 1H, J$_1$=1.6 Hz, J$_2$=8.0 Hz) ppm. At room temperature, compound exists as a mixture of cis/trans amide rotamers, ca. 1:1 by $^1$H NMR (d$_6$-DMSO; T=25° C.) δ 4.75 (q, 0.9H, J=7.2 Hz) & 5.23 (q, 1.0 H, J=7.2 Hz) ppm. MS (ESI$^+$) 549.3 [MH]$^+$.

Example 3

This example illustrates the preparation of Compound 3.1

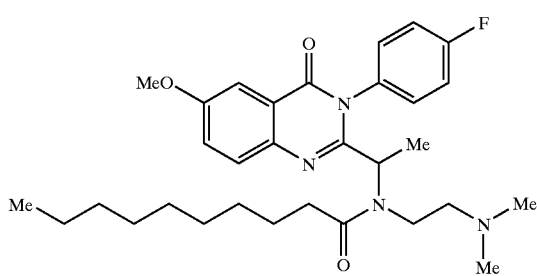

3.1

3.1 Preparation of 5-methoxy-2-propionylamino-benzoic acid (f) from 2-amino-5-methoxy-benzoic acid

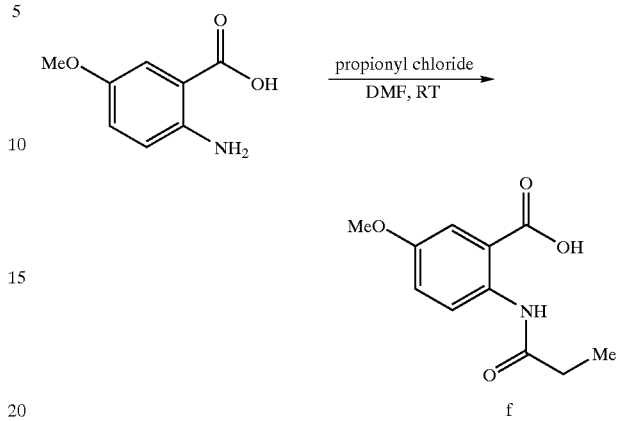

To a room temperature solution of 5.068 g 2-amino-5-methoxy-benzoic acid (30.3 mmol, 1.00 equiv) dissolved in 25 mL dry DMF was added 2.90 mL propionyl chloride (33.3 mmol, 1.10 equiv) dropwise by addition funnel over a period of 45 minutes. Upon completed addition of the acid chloride, the heterogeneous reaction mixture was stirred for 14 hours at room temperature and then poured into 300 mL water. The resulting water/DMF mixture, with white precipitate, was stirred vigorously at ambient temperature for one hour, after which time the solid was collected by vacuum filtration, rinsing the solid with cold water (2×50 mL). The white solid was dried in vacuo over phosphorous pentoxide overnight to afford 5.17 g of f as a white solid; 76% yield. m.p. 139.7° C. $^1$H NMR (CDCl$_3$) δ 1.32 (t, 3H, J=7.6 Hz), 2.53 (q, 2H, J=7.6 Hz), 3.86 (s, 3H), 7.24 (dd, 1H, J$_1$=3.0 Hz, J$_2$=9.2 Hz), 7.63 (d, 1H, J=3.0 Hz), 8.70 (d, 1H, J=9.2 Hz), 10.80 (s, 1H) ppm. MS (ESI$^-$) 222.1 [M−H]$^{31}$.

3.2 Preparation of 2-ethyl-3-(4-fluorophenyl)-6-methoxy-3H-quinazolin-4-one (g) from 5-methoxy-2-propionylamino-benzoic acid (f)

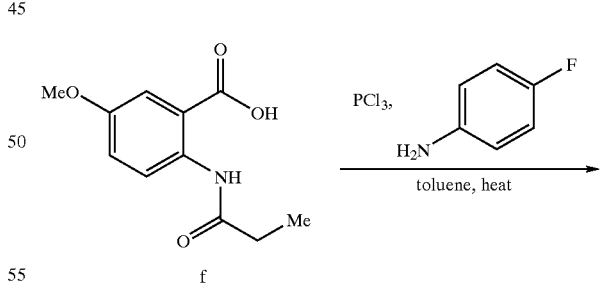

To a mixture of 2.036 g f (9.12 mmol, 1.00 equiv) and 1.013 g 4-fluoroaniline (9.12 mmol, 1.00 equiv) suspended in 18 mL toluene was added a solution of 0.358 mL phosphorous trichloride (4.10 mmol, 0.450 equiv) dissolved in 5 mL toluene dropwise by addition funnel over a period of 15 minutes. The resulting heterogeneous mixture was heated to reflux for 6 hours, alter which time TLC indicated no f remained ($R_f$=0.15, 40% ethyl acetate in hexane). To the room temperature reaction mixture was added 30 mL aqueous 10% sodium carbonate solution and the resulting biphase was stirred vigorously until all solids dissolved. The toluene was removed in vacuo and a precipitate developed. The solid was collected by filtration, rinsing with water (2×50 mL). The air-dried solid was purified by recrystallization from isopropyl alcohol to afford 1.945 g of g as colorless needles, dried in vacuo over phosphorous pentoxide; 72% yield. m.p. 153.7° C. $^1$H NMR (CDCl$_3$) δ 1.24 (t, 3H, J=7.6 Hz), 2.44 (q, 2H, J=7.6 Hz), 3.93 (s, 3H), 7.28 (2×d, 2×2H, J=4.4 Hz), 7.40 (dd, 1H, $J_1$=2.8 Hz, $J_2$=9.2 Hz), 7.65 (d, 1H, J=2.8 Hz), 7.68 (d, 1H, J=9.2 Hz) ppm. MS (ESI$^+$) 299.1 [MH]$^+$.

3.3 Preparation of 2-(1-bromoethyl)-3-(4-fluorophenyl)-6-methoxy-3H-quinazolin-4-one (h) from 2-ethyl-3-(4-fluorophenyl)-6-methoxy-3H-quinazolin-4-one (g)

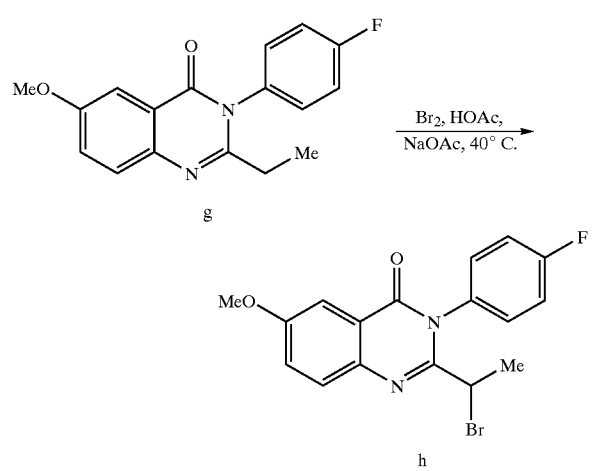

To a mixture of 1.016 g g (3.406 mmol, 1.000 equiv) and 0.335 g sodium acetate (4.09 mmol, 1.20 equiv) in 20 mL glacial acetic acid at 40° C. (external temperature, oil bath) was added a solution of 0.175 mL bromine (3.41 mmol, 1.00 equiv) dissolved in 3 mL glacial acetic acid dropwise by addition funnel over a period of 30 minutes. After 3.5 hours, TLC indicated no g remained ($R_f$=0.33, 33% ethyl acetate in hexane) and the reaction solution was poured into 250 mL water. The resulting mixture was stirred vigorously at room temperature for 2 hours, after which time the precipitate was collected by vacuum filtration, rinsing with warm (ca. 40° C.) water (2×50 mL). The solid was dried in vacuo over phosphorous pentoxide overnight, affording 1.103 g of h. as a white solid; 86% yield. m.p. 166.4° C. $^1$H NMR (CDCl$_3$) δ 2.08 (d, 3H, J=6.7 Hz), 3.94 (s, 3H), 4.58 (q, 1H, J=6.7 Hz), 7.18 (ddd, 1H, $J_1$=2.7 Hz, $J_2$=4.7 Hz, $J_3$8.4 Hz), 7.29 (ddt, 2H, $J_1$=2.9 Hz, $J_2$=8.2 Hz, $J_3$=17.7 Hz), 7.42 (dd, 1H, $J_1$=2.9 Hz, $J_2$=8.9 Hz), 7.59 (ddd, $J_1$=2.7 Hz, $J_2$=4.8 Hz, $J_3$=5.4 Hz), 7.66 (d, 1H, J=2.9 Hz). 7.76 (d, 1H, J=8.9 Hz) ppm. MS (ESI$^+$) 377.0 [MH]$^+$.

3.4 Preparation of 2-[1-(2-dimethylaminoethylamino)-ethyl]-3-(4-flurophenyl)-6-methoxy-3H-quinazolin-4-one (j) from 2-(1-bromoethyl)-3-(4-fluorophenyl)-6-methoxy-3H-quinazolin-4-one (h)

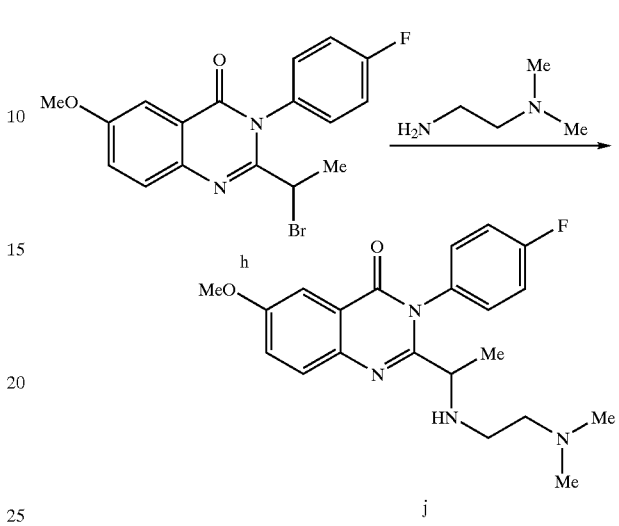

A mixture of 0.273 g h (0.724 mmol, 1.00 equiv) and 0.127 mL 2-(dimethylamino)-1-aminoethane (1.16 mmol, 1.60 equiv) in 6 mL ethanol was heated to reflux for 23 hours, after which time TLC indicated no h remained ($R_f$=0.73, 40% ethyl acetate in hexane). The ethanol was removed in vacuo and the concentrate partitioned between dichloromethane (30 mL) and saturated aqueous sodium bicarbonate solution (25 mL). The separated aqueous layer was extracted again with dichloromethane (30 mL) and the combined organic extracts dried over sodium sulfate, filtered, and concentrated in vacuo to yield a yellow glass. The crude material was purified by chromatography on silica gel (3.5 cm o.d.×12 cm h) eluting with 5% methanol in chloroform. Fractions containing product at $R_f$=0.16 (10% methanol in chloroform) were combined and concentrated in vacuo to afford 260 mg of j as a pale yellow, glassy solid; 94% yield. m.p. 124.8° C. $^1$H NMR (CDCl$_3$) δ 1.26 (d, 3H, J=6.8 Hz), 2.20 (s, 6H), 2.23 (dt, 1H, $J_1$=4.8 Hz, $J_2$=11.6 Hz), 2.42 (dt, 1H, $J_1$=4.8 Hz, $J_2$=10.0 Hz), 2.49–2.54 (m, 1H), 2.57–2.63 (m, 1H), 2.71 (br s, 1H), 3.42 (q, 1H, J=6.8 Hz), 3.91 (s, 3H), 7.23–7.28 (m, 4H), 7.37 (dd, 1H, $J_1$=2.8 Hz, $J_2$=8.8 Hz), 7.62 (d, 1H, J=3.2 Hz), 7.66 (d, 1H, J=8.8 Hz) ppm. MS (ESI$^+$) 385.2 [MH]$^+$.

3.5 Preparation of 3.1 from 2-[1-(2-dimethylaminoethylamino)-ethyl]-3-(4-fluorophenyl)-6-methoxy-3H-quinazolin-4-one (j)

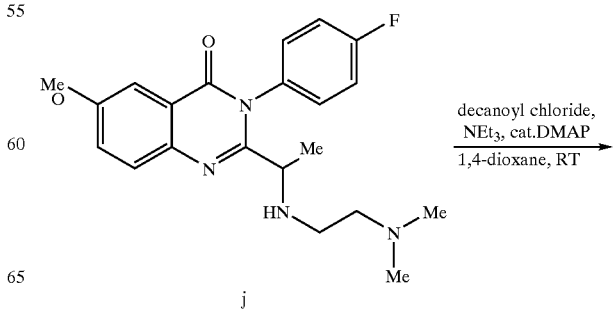

-continued

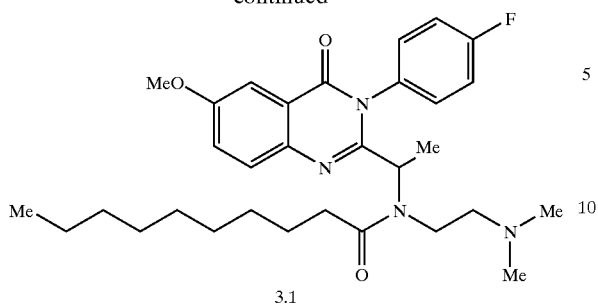

3.1

To a room temperature solution of 120 mg j (0.313 mmol, 1.00 equiv), 0.048 mL triethylamine (0.345 mmol, 1.10 equiv), and 2.0 mg DMAP (0.016 mmol, 0.052 equiv) dissolved in 2 mL 1,4-dioxane was added 0.065 mL decanoyl chloride (0.313 mmol, 1.00 equiv); a colorless precipitate developed. The reaction mixture was stirred overnight at room temperature then concentrated in vacuo to remove the dioxane. The resulting concentrate was partitioned between dichloromethane and aqueous saturated sodium bicarbonate solution (25 mL each). The separated aqueous layer was extracted again with dichloromethane (25 mL) and the combined organic extracts dried over sodium sulfate, filtered, and concentrated in vacuo to yield a yellow, glassy oil. The crude product was purified by chromatography on silica gel (3.5 cm o.d.×8 cm h) eluting with 3% methanol in chloroform. Fractions containing product at $R_f$=0.42 (10% methanol in chloroform) were combined and concentrated in vacuo to afford 104 mg of 3.1 as a white solid; 62% yield. m.p. 120.2° C. $^1$H NMR (d$_6$-DMSO; T=140° C.) δ 0.90 (t, 3H, J=6.8 Hz), 1.18–1.48 (m, 14H), 1.44 (d, 3H, J=6.8 Hz), 1.94–2.06 (m, 2H), 2.05 (s, 6H), 2.13–2.21 (m, 1H), 2.36–2.44 (m, 1H), 3.25 (ddd, 1H, $J_1$=5.2 Hz, $J_2$=8.8 Hz, $J_3$=14.4 Hz), 3.39 (ddd, 1H, $J_1$=6.0 Hz, $J_2$=9.2 Hz, $J_3$=15.2 Hz), 3.91 (s, 3H), 5.10 (br m, 1H), 7.30 (br m, 3H), 7.46 (d, 1H, J=2.8 Hz), 7.48 (d, 1H, J=2.8 Hz), 7.57 (d, 1H, J=2.8 Hz), 7.69 (d, 1H, J=8.8 Hz) ppm. At room temperature, compound exists as a mixture of cis/trans amide rotamers, ca. 1:1 by $^1$H NMR (d$_6$-DMSO; T=25° C.) δ 4.75 (q, 1.0H, J=6.8 Hz) & 5.25 (q, 1.0H, J=6.8 Hz) ppm. MS (ESI$^+$) 539.5 [MH]$^+$.

Example 4

This example illustrates the preparation of additional compounds using the methodology provided in Example 3.

Preparation of 4.1

Compound 4.1

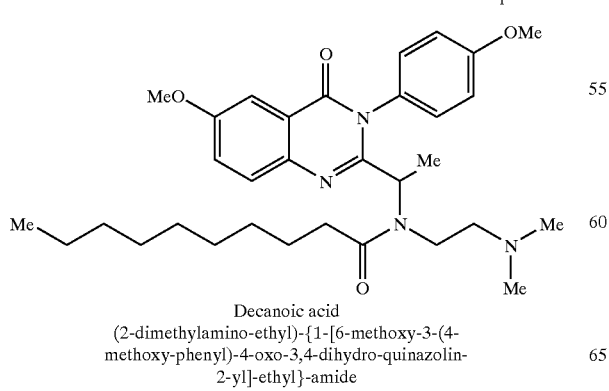

Decanoic acid
(2-dimethylamino-ethyl)-{1-[6-methoxy-3-(4-methoxy-phenyl)-4-oxo-3,4-dihydro-quinazolin-2-yl]-ethyl}-amide Compound 4.1 was prepared following the synthesis of 3.1 described above, with the exception that 4-methoxyaniline was used in place of 4-fluoroaniline. Characterization data for 4.1 follows: white solid, m.p. 124.2° C. MS (ESI$^+$) 551.5 [MH]$^+$.

Preparation of 4.2

(Compound 4.2)

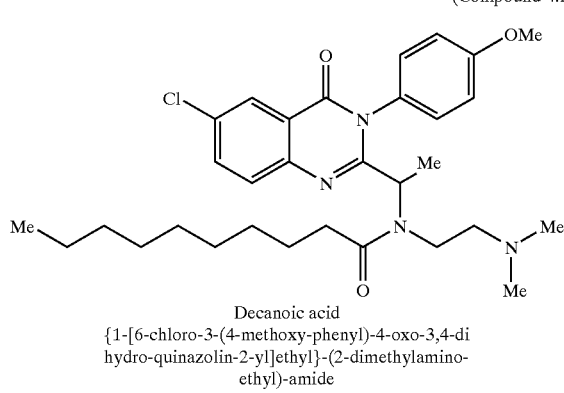

Decanoic acid
{1-[6-chloro-3-(4-methoxy-phenyl)-4-oxo-3,4-di hydro-quinazolin-2-yl]ethyl}-(2-dimethylamino-ethyl)-amide Compound 4.2 was prepared following the synthesis of 3.1 described above, with the exception that 2-amino-6-chloro-benzoic acid was used in place of 2-amino-6-methoxy-benzoic acid and 4-methoxyaniline was used in place of 4-fluoroaniline. Characterization data for 4.2 follows: pale yellow, low-melting solid. MS (ESI$^+$) 555.3 [MH]$^+$ Preparation of 4.3

(Compound 4.3)

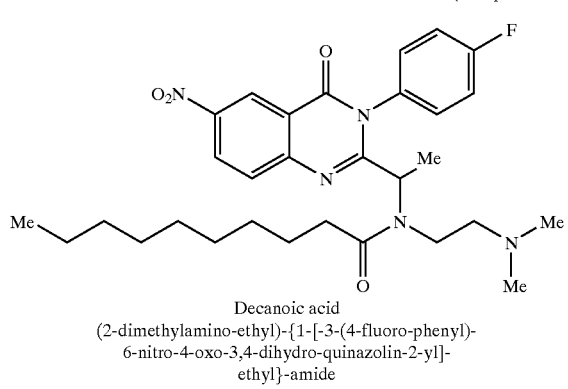

Decanoic acid
(2-dimethylamino-ethyl)-{1-[-3-(4-fluoro-phenyl)-6-nitro-4-oxo-3,4-dihydro-quinazolin-2-yl]-ethyl}-amide Compound 4.3 was prepared following the synthesis of 3.1 described above, with the exception that 2-amino-6-nitro-benzoic acid was used in place of 2-amino-6-methoxy-benzoic acid. Characterization data for 4.3 follows: orange oil. MS (ESI$^+$) 554.3 [MH]$^+$ Preparation of 4.4

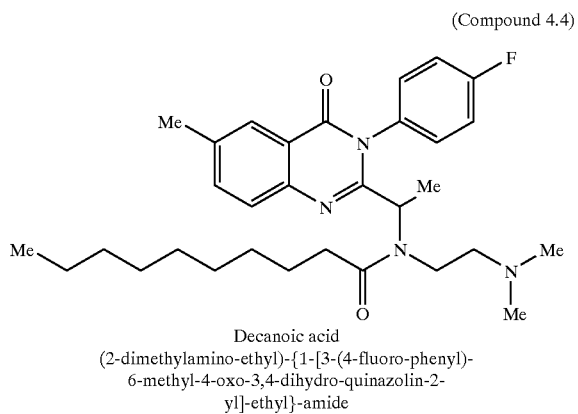

Decanoic acid
(2-dimethylamino-ethyl)-{1-[3-(4-fluoro-phenyl)-
6-methyl-4-oxo-3,4-dihydro-quinazolin-2-
yl]-ethyl}-amide Compound 4.4 was prepared following the synthesis of 3.1 described above, with the exception that 2-amino-5-methyl-benzoic acid was used in place of 2-amino-5-methoxy-benzoic acid. Characterization data for 4.4 follows: white solid, m.p. 121.0° C. MS (ESI$^+$) 523.4 [MH]$^+$.

Preparation of Compound 4.5

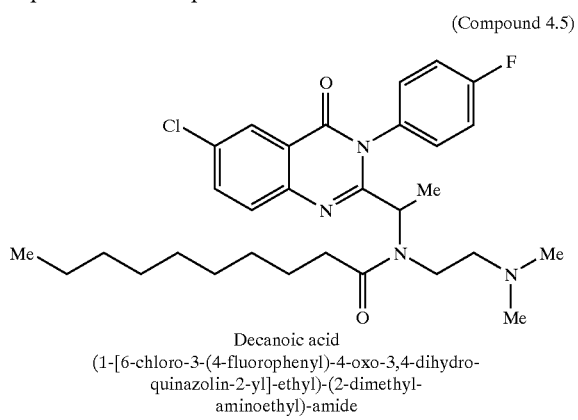

Decanoic acid
(1-[6-chloro-3-(4-fluorophenyl)-4-oxo-3,4-dihydro-
quinazolin-2-yl]-ethyl)-(2-dimethyl-
aminoethyl)-amide Compound 4.5 was prepared following the synthesis of 3.1 described above, with the exception that 2-amino-5-chloro-benzoic acid was used in place of 2-amino-5-methoxy-benzoic acid. Characterization data for 4.5 follows: white solid m.p. 122.9° C. MS (ESI$^+$) 543.3 [MH]$^+$.

Preparation of Compound 4.6

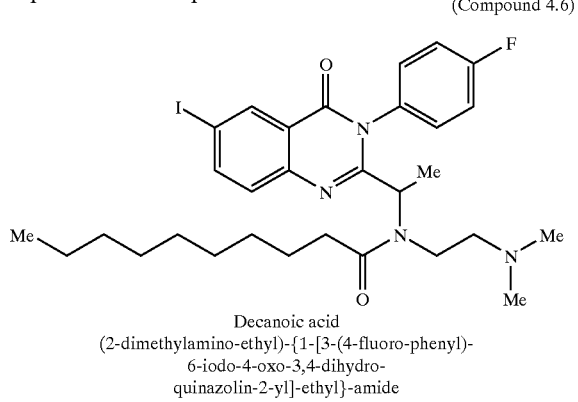

Decanoic acid
(2-dimethylamino-ethyl)-{1-[3-(4-fluoro-phenyl)-
6-iodo-4-oxo-3,4-dihydro-
quinazolin-2-yl]-ethyl}-amide Compound 4.6 was prepared following the synthesis of 3.1 described above, with the exception that 2-amino-5-iodo-benzoic acid was used in place of 2-amino-5-methoxy-benzoic acid. Characterization data for 4.6 follows: pale yellow, low-melting solid. MS (ESI$^+$) 635.3 [MH]$^+$.

Preparation of Compound 4.7

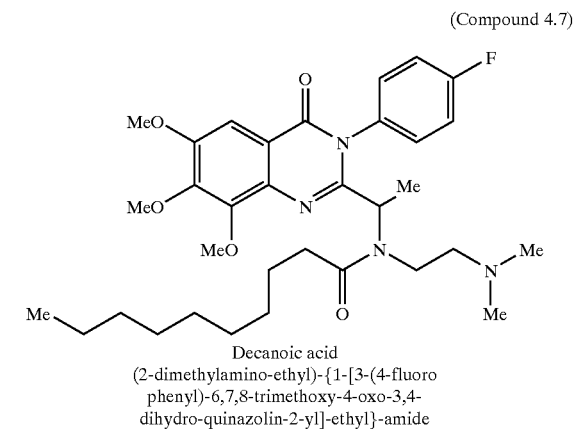

Decanoic acid
(2-dimethylamino-ethyl)-{1-[3-(4-fluoro
phenyl)-6,7,8-trimethoxy-4-oxo-3,4-
dihydro-quinazolin-2-yl]-ethyl}-amide Compound 4.7 was prepared following the synthesis of 3.1 described above, with the exception that 2-amino-3,4,5-trimethoxy-benzoic acid was used in place of 2-amino-5-methoxy-benzoic acid. Characterization data for 4.7 follows: pale yellow solid, m.p. 106.7° C. MS (ESI$^+$) 599.5 [MH]$^+$.

Preparation of Compound 4.8

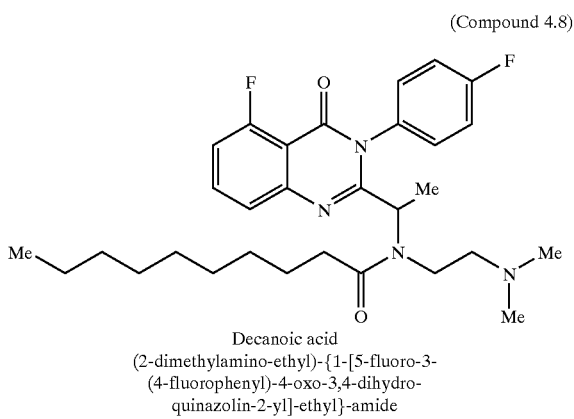

Decanoic acid
(2-dimethylamino-ethyl)-{1-[5-fluoro-3-
(4-fluorophenyl)-4-oxo-3,4-dihydro-
quinazolin-2-yl]-ethyl}-amide Compound 4.8 was prepared following the synthesis of 3.1 described above, with the exception that 2-amino-6-fluoro-benzoic acid was used in place of 2-amino-5-methoxy-benzoic acid. Characterization data for 4.8 follows: colorless viscous oil. MS (ESI$^+$) 527.3 [MH]$^+$.

Example 5

This example illustrates the preparation of Compound 5.1 from Compound 4.6.

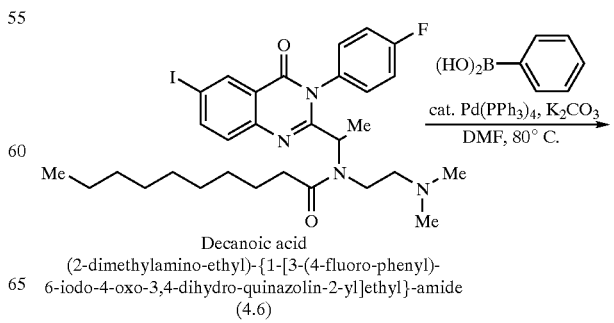

Decanoic acid
(2-dimethylamino-ethyl)-{1-[3-(4-fluoro-phenyl)-
6-iodo-4-oxo-3,4-dihydro-quinazolin-2-yl]ethyl}-amide
(4.6)

-continued

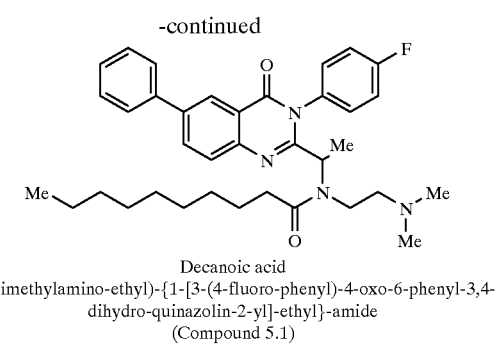

Decanoic acid
(2-dimethylamino-ethyl)-{1-[3-(4-fluoro-phenyl)-4-oxo-6-phenyl-3,4-
dihydro-quinazolin-2-yl]-ethyl}-amide
(Compound 5.1)

A resealable Schlenck reaction flask was charged with 32 mg 4.6 (50 umol, 1.0 equiv), 14 mg potassium carbonate (100 umol, 2.0 equiv), 10 mg phenylboronic acid (82 umol, 1.6 equiv), 10 mg tetrakis(triphenylphosphine)palladiuin(0) (8.7 umol, 0.17 equiv), and 2.0 mL DMF. The mixture was degassed by freeze-evacuate-thaw (3 cycles) then opened to nitrogen atmosphere and heated to 80° C. (external temperature, oil bath) for 2 hours, after which time MS and TLC indicated no 4.6 remained ([MH]$^+$=635.3; R$_f$=0.26, 6% methanol in chloroform). The DMF was removed in vacuo and the concentrate adsorbed onto a column of silica gel (2.5 cm o.d.×12 cm h) and eluted with 3% methanol in chloroform. Fractions containing product were combined and concentrated in vacuo to afford 23 mg of 5.1 as a colorless oil; 79% yield. MS (ESI$^+$) 585.3 [MH]$^+$.

Example 6

This example illustrates the preparation of Compound 6.1 from Compound 4.6.

A resealable Schlenck reaction flask was charged with 17 mg 4.6 (26 umol, 1.0 equiv), 15 uL phenylacetylene (135 umol, 5.2 equiv), 2.0 mg bis(triphenylphosphine)palladiuin (II) dichloride (2.7 umol, 0.1 equiv), 1.0 mg copper(I) iodide (4.0 umol, 0.15 equiv), and 3.0 mL triethylamine. The mixture was degassed by freeze-evacuate-thaw (3 cycles) then opened to nitrogen atmosphere and stirred at room temperature. After 1.5 hours, MS indicated no 4.6 remained and the reaction was concentrated in vacuo then adsorbed onto a column of silica gel (2.5 cm o.d.×10 cm h) and eluted with 3% methanol in chloroform. Fractions containing product were combined and concentrated in vacuo to afford 16 mg of 6.1 as a colorless oil; 98% yield. MS (ESI$^+$) 609.3 [MH]$^+$.

Example 7

This example illustrates the preparation of Compound 7.1 from Compound 6.1.

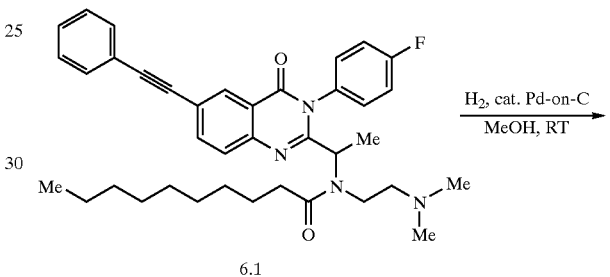

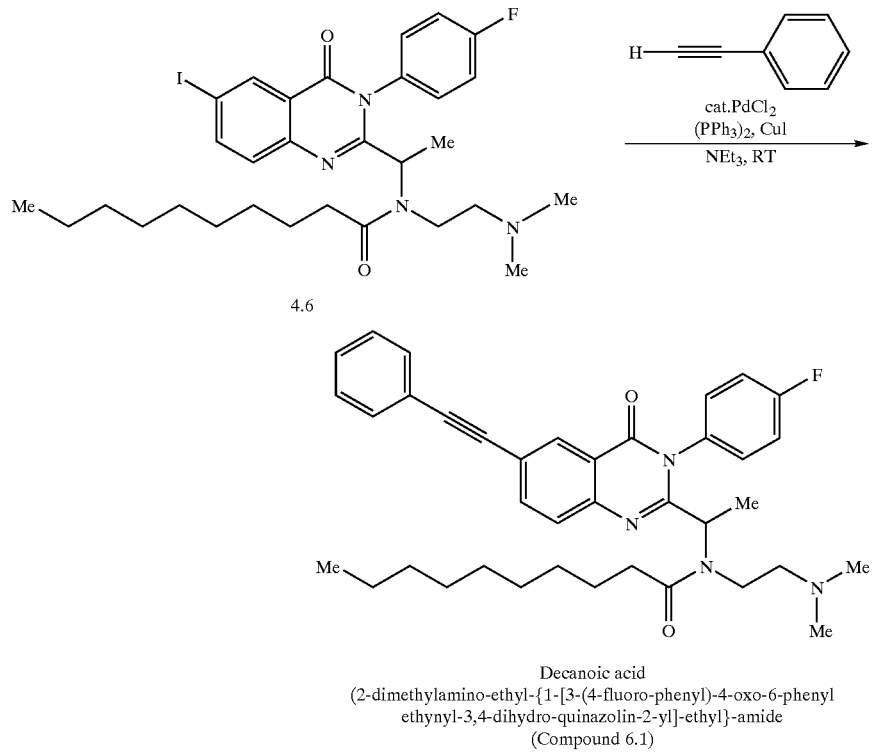

Decanoic acid
(2-dimethylamino-ethyl-{1-[3-(4-fluoro-phenyl)-4-oxo-6-phenyl
ethynyl-3,4-dihydro-quinazolin-2-yl]-ethyl}-amide
(Compound 6.1)

-continued

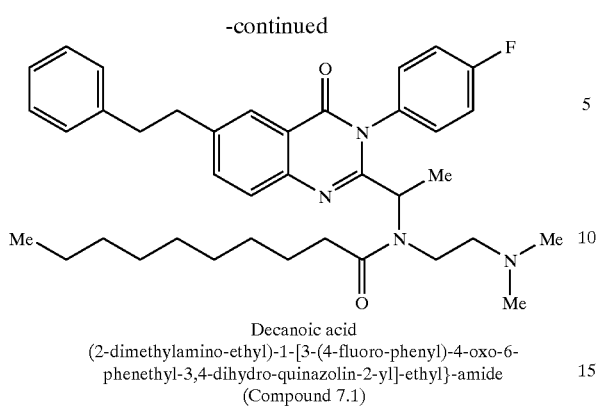

Decanoic acid
(2-dimethylamino-ethyl)-1-[3-(4-fluoro-phenyl)-4-oxo-6-
phenethyl-3,4-dihydro-quinazolin-2-yl]-ethyl}-amide
(Compound 7.1)

Hydrogen gas was introduced (by balloon) to a nitrogen-purged flask charged with 8.2 mg of 6.1 (13 umol, 1.0 equiv), 14 mg palladium on activated carbon (10% wt. Pd; 13 umol, equiv), and 3.0 mL methanol. The reaction mixture was stirred at room temperature for 16 hours then filtered through a pad of Celite. The filtrate was concentrated in vacuo to afford a faint yellow film. The crude product was purified by column chromatography on silica gel (2.5 cm o.d.×10 cm h) eluting with 3% methanol in chloroform. Fractions containing product at $R_f$=0.29, 6% methanol chloroform, were combined and concentrated in vacuo to afford 6.6 mg of 7.1 as a colorless film 80% yield. MS (ESI$^+$) 613.4 [MH]$^+$.

Example 8

This example illustrates the preparation of Compound 8.1 from Compound 4.3.

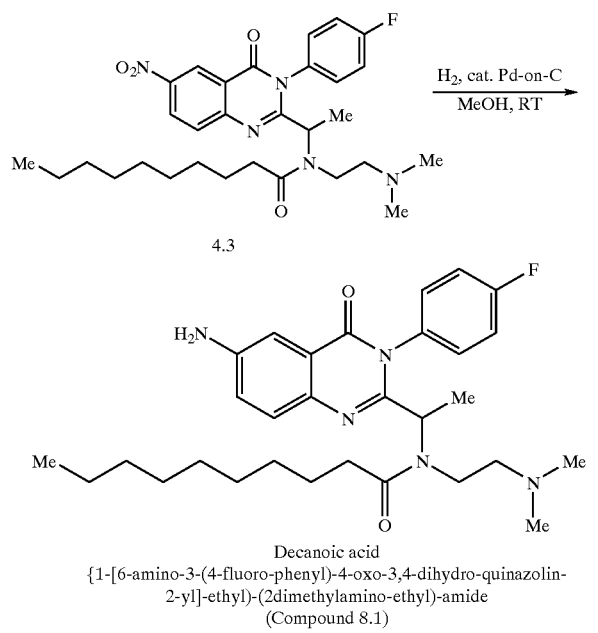

Decanoic acid
{1-[6-amino-3-(4-fluoro-phenyl)-4-oxo-3,4-dihydro-quinazolin-
2-yl]-ethyl)-(2dimethylamino-ethyl)-amide
(Compound 8.1)

Hydrogen gas was introduced (by balloon) to a nitrogen-purged flask charged with 12.8 mg 4.3 (23 umol, 1.0 equiv), 12 mg palladium on activated carbon (10% wt. Pd; 12 umol, 0.52 equiv), and 4.0 mL methanol. The reaction mixture was stirred at room temperature for 16 hours then filtered through a pad of Celite. The filtrate was concentrated in vacuo to afford a yellow-orange film. The crude product was purified by column chromatography on silica gel (2.5 cm o.d.×10 cm h) eluting with 5% methanol in chloroform. Fractions containing product at $R_f$=0.11, 10% methanol in chloroform, were combined and concentrated in vacuo to afford 5.8 mg of 8.1 as a colorless film; 48% yield. MS (ESI$^+$) 524.3 [MH]$^+$.

Example 9

This example illustrates screening procedures used in characterizing the compounds of the present invention.

Source plates of chemical libraries were obtained from commercial vendors and contained individual compounds at 5 mg/mL in DMSO, or in some instances, at 1 mg/mL. From these, multiple compound plates containing 10 compounds in each well were made, and these were diluted in 20% DMSO to a concentration of 50 µg/mL (10 µg/mL for those beginning at 1 mg/mL). An aliquot of 20 µL of each mixture was put into the test plates, which were stored frozen until use.

CXCR3-expressing cells were prepared according to standard methods and used in most assays. The cells were cultured in IMDM-5% FBS, and harvested when the concentration was between 0.5–1.0×10$^6$ cells/mL. The cells were centrifuged and resuspended in assay buffer (20 mM HEPES, 80 mM NaCl, 1 mM CaCl$_2$, 5 mM MgCl$_2$, and with 0.2% bovine serum albumin, pH 7.1) to a concentration of 5.6×10$^6$ cells/mL. Using a Multi-Probe automated system, 0.09 mL of cells was added to each well of the assay test plates containing the compounds, followed by 0.09 mL of $^{125}$I-IP-10 (from New England Nuclear) diluted in assay buffer (final concentration ~25–100 pM, with ~50,000 cpm per well). The final concentration of the compounds was 1–5 µg/mL each. The plates were sealed and incubated for approximately 3 hours at 4° C. on a shaker platform. (In some experiments radiolabeled MIG was used.) The assay plates were harvested using Packard filter plates, pre-soaked in PEI solution, on the vacuum harvest apparatus. Scintillation fluid (35 µL) was added to each of the wells, the plates were sealed and counted in a Top Count scintillation counter. Control wells contained either diluent only (for total counts) or excess IP-10 (1 µg/mL, for non-specific binding) and were used to calculate the percent of total inhibition for each set of compounds. Further tests on individual compounds were carried out in the same manner. IC$_{50}$ values are those concentrations required to reduce the binding of labeled IP-10 to the receptor by 50%.

Calcium mobilization assays were performed by labeling human peripheral blood lymphocytes (cultured in 10 ng/mL IL-2 for at least 12 days) with INDO-1 dye (45 min at room temperature), washing with PBS, and resuspending into flux buffer (HBSS with 1% fetal bovine serum). For each test, 1×10$^6$ cells were incubated at 37° C. in the cuvette of a PTI spectrometer, and the ratio of 400/490 nm emission was plotted over time (typically 2–3 minutes), with compounds added at 5 seconds, followed by IP-10 or other chemokines.

Chemotaxis assays were performed using 5 µm filter plates (Neuroprobe) with the chemoattractant placed in the lower chamber, and a cell suspension of 50,000 to 100,000 cells in the upper chamber. The assays were incubated 1–2 hours at 37° C., and the number of cells in the lower chamber quantified using a CyQuant assay (Molecular Probes).

The binding of IP-10 or MIG to CXCR3 was first optimized by testing various pH and salt concentrations for their effect in a homologous competition assay. Maximum binding of radiolabeled MIG takes place under low salt (80 mM) conditions, as compared to normal salt (140 mM), while there is no difference between pH 7.1 and 7.4.

Example 10

This example provides a table of compounds prepared using methods similar to those provided in Example 1, and evaluated using the methods described in Example 2. In the table below, activity is reported as follows: +, $IC_{50}>5$ $\mu M$; ++, 5 $\mu M \geq IC_{50}>0.8$ $\mu M$; +++, $IC_{50} \leq 0.8$ $\mu M$.

TABLE 1

| Compound | $R^1$ | —Y—Z | Ar | Activity $IC_{50}$ |
|---|---|---|---|---|
| 1.1 | hexanoyl | —(CH$_2$)$_2$N(CH$_3$)$_2$ | 4-fluorophenyl | + |
| 1.2 | heptanoyl | " | " | + |
| 1.3 | heptanoyl | " | 4-methoxyphenyl | ++ |
| 1.4 | octanoyl | " | 4-bromophenyl | ++ |
| 1.5 | octanoyl | " | 4-methoxyphenyl | ++ |
| 1.6 | octanoyl | " | 4-fluorophenyl | ++ |
| 1.7 | nonanoyl | " | 4-methylphenyl | + |
| 1.8 | nonanoyl (branched) | " | 4-fluorophenyl | + |
| 1.9 | nonanoyl | " | 4-methoxyphenyl | +++ |
| 1.10 | nonanoyl | " | 4-chlorophenyl | +++ |
| 1.11 | decanoyl | " | 4-fluorophenyl | +++ |
| 1.12 | decanoyl | " | phenyl | + |
| 1.13 | dodecanoyl | " | 4-chlorophenyl | ++ |
| 1.14 | tetradecanoyl | " | 4-fluorophenyl | +++ |
| 1.15 | tetradecanoyl | " | 4-methoxyphenyl | +++ |

In addition, compound 1.11 was tested against 5 other chemokine receptors on activated lymphocytes, and did not interfere with signalling by those chemokines.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

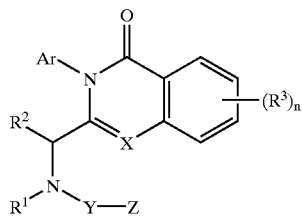

wherein,
the subscript n is an integer of from 0 to 4;
Ar is a member selected from the group consisting of substituted or unsubstituted aryl and substituted or unsubstituted heteroaryl, wherein each substituent of the substituted aryl or substituted heteroaryl is independently selected from the group consisting of halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, wherein R', R" and R'" are independently selected from hydrogen, (C$_1$–C$_8$)alkyl and heteroalkyl, unsubstituted aryl and heteroaryl, unsubstituted aryl-(C$_1$–C$_4$)alkyl, and unsubstituted aryloxy-(C$_1$–C$_4$)alkyl; and optionally further wherein two of the substituents on adjacent atoms of the aryl or heteroaryl ring may be replaced with a substituent of the formula -T-C(O)—(CH$_2$)$_q$-U-, wherein T and U are independently —NH—, —O—, —CH$_2$— or a single bond, and q is an integer of from 0 to 2, or a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3, and wherein one of the single bonds of the ring so formed may optionally be replaced with a double bond, or a substituent of the formula —(CH$_2$)$_s$—X—(CH$_2$)$_t$—, where s and t are independently integers of from 0 to 3, and X is —O—, —NR'"—, —S—, —S(O)—, —S(O)$_2$—, or —S(O)$_2$NR'"— and the substituent R'" in —NR'"— and —S(O)$_2$NR'"— is selected from hydrogen or unsubstituted (C$_1$–C$_6$)alkyl;
$R^1$ is a member selected from the group consisting of substituted or unsubstituted (C$_5$–C$_{15}$)alkyl and (C$_8$–C$_{14}$)acyl group;
$R^2$ is a member selected from the group consisting of substituted or unsubstituted (C$_1$–C$_8$)alkyl;
each $R^3$ is independently a substituent selected from the group consisting of halogen, —OR$^b$, —OC(O)R$^b$, —NR$^b$R$^c$, —SR$^b$, —R$^b$, —CN, —NO$_2$, —CO$_2$R$^b$, —CONR$^b$R$^c$, —C(O)R$^b$, —OC(O)NR$^b$R$^c$, —NR$^c$C(O)R$^b$, —NR$^c$C(O)$_2$R$^b$, —NR$^b$—C(O)NR$^c$R$^d$, —NH—C(NH$_2$)=NH, —NR$^b$—C(NH$_2$)=NH, —NH—C(NH$_2$)=NR$^b$, —S(O)R$^b$, —S(O)$_2$R$^b$, —S(O)$_2$NR$^b$R$^c$, —N$_3$, —CH(Ph)$_2$, perfluoro(C$_1$–C$_4$)alkoxy, and perfluoro(C$_1$–C$_4$)alkyl, and where R$^b$, R$^c$ and R$^d$ are independently selected from hydrogen, (C$_1$–C$_8$)alkyl and heteroalkyl, unsubstituted aryl and heteroaryl, unsubstituted aryl-(C$_1$–C$_4$)alkyl, and unsubstituted aryloxy-(C$_1$–C$_4$)alkyl;
Y is a member selected from the group consisting of substituted or unsubstituted (C$_2$–C$_8$)alkylene and substituted or unsubstituted (C$_2$–C$_8$)heteroalkylene;
Z is —NR$^4$R$^5$,
$R^4$ and $R^5$ are independently selected from the group consisting of hydrogen and (C$_1$–C$_8$)alkyl or taken together with the nitrogen atom to which each is attached to form a heterocyclyl with 5, 6, or 7 members or a heteroaryl; and,
each of said substituted alkyl, heteroalkyl, alkylene or heteroalkylene of Y, $R^1$, $R^2$ is independently substituted with one or members independently selected from the group consisting of —OR$^e$, =O, =NR$^e$, =N—OR$^e$, —NR$^e$R$^f$, —SR$^e$, halogen, —Sir$^e$R$^f$R$^g$,

39

—OC(O)R$^e$, —C(O)R$^e$, —CO$_2$R$^e$, —CONR$^e$R$^f$, —OC(O)NR$^e$R$^f$, —NR$^f$C(O)R$^e$, —NR$^e$—C(O)NR$^f$R$^g$, —NR$^f$C(O)$_2$R$^e$, —NH—C(NH$_2$)=NH, —NR$^e$C(NH$_2$)=NH, —NH—C(NH$_2$)=NR$^e$, —S(O)R$^e$, —S(O)$_2$R$^e$, —S(O)$_2$NR$^e$, —R$^f$, —CN and —NO$_2$ in a number ranging from zero to (2m'+1), wherein m' is the total number of carbon atoms in said alkyl, heteroalkyl, alkylene or heteroalkylene of said substituted alkyl, heteroalkyl, alkylene or heteroalkylene of Y, R$^1$, and R$^2$; and R$^e$, R$^f$ and R$^g$ each independently is hydrogen, unsubstituted (C$_1$–C$_8$)alkyl and heteroalkyl, unsubstituted aryl, aryl substituted with from 1 to 3 halogens, unsubstituted alkyl, alkoxy or thioalkoxy groups, or aryl-(C$_1$–C$_4$)alkyl groups; and optionally, when R$^e$ and R$^f$ are attached to the same nitrogen atom, R$^e$ and R$^f$ can be taken together with the nitrogen atom to form a heterocyclyl with 5, 6, or 7 members or a heteroaryl.

2. A compound in accordance with claim 1, wherein Ar is substituted phenyl.

3. A compound in accordance with claim 1, wherein Ar is substituted phenyl, and R$^1$ is a (C$_8$–C$_{14}$)acyl group.

4. A compound in accordance with claim 1, wherein Ar is substituted phenyl, R$^1$ is a (C$_8$–C$_{14}$)acyl group, and R$^2$ is unsubstituted (C$_1$–C$_4$)alkyl.

5. A compound in accordance with claim 1, wherein Ar is substituted phenyl, R$^1$ is a (C$_8$–C$_{14}$)acyl group, R$^2$ is unsubstituted (C$_1$–C$_4$)alkyl, and Y is (C$_2$–C$_5$)alkylene.

6. A compound in accordance with claim 1, wherein Ar is substituted phenyl, R$^1$ is a (C$_8$–C$_{14}$)acyl group, R$^2$ is unsubstituted (C$_1$–C$_4$)alkyl, Y is (C$_2$–C$_5$)alkylene, and Z is dimethylamino.

7. A compound in accordance with claim 1, wherein Ar is substituted phenyl, R$^1$ is a (C$_8$–C$_{14}$)acyl group, R$^2$ is unsubstituted (C$_1$–C$_4$)alkyl, Y is (C$_2$–C$_5$)alkylene, Z is dimethylamino, and n is 0.

8. A compound in accordance with claim 1, wherein Ar is substituted phenyl, R$^1$ is a (C$_8$–C$_{14}$)acyl group, R$^2$ is methyl, Y is ethylene, Z is dimethylamino, and n is 0.

9. A compound in accordance with claim 8, wherein said substituted phenyl is selected from the group consisting of 4-fluorophenyl, 4-methoxyphenyl, 4-chlorophenyl, 4-methylphenyl, and 4-bromophenyl.

10. A composition comprising a pharmaceutically acceptable excipient and a compound having the formula:

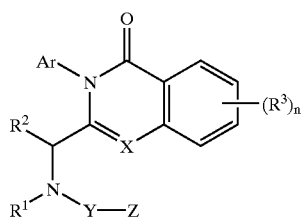

where,
the subscript n is an integer of from 0 to 4;
Ar is a member selected from the group consisting of substituted or unsubstituted aryl and substituted or unsubstituted heteroaryl, wherein each substituent of the substituted aryl or substituted heteroaryl is independently selected from the group consisting of halogen, —OR', —OC(O)R', —NR'R", —SR', —R', —CN, —NO$_2$, —CO$_2$R', —CONR'R", —C(O)R',

40

—OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, wherein R', R" and R'" are independently selected from hydrogen, (C$_1$–C$_8$)alkyl and heteroalkyl, unsubstituted aryl and heteroaryl, unsubstituted aryl-(C$_1$–C$_4$)alkyl, and unsubstituted aryloxy-(C$_{1-4}$)alkyl; and optionally further wherein two of the substituents on adjacent atoms of the aryl or heteroaryl ring may be replaced with a substituent of the formula -T-C(O)—(CH$_2$)$_q$-U-, wherein T and U are independently —NH—, —O—, —CH$_2$— or a single bond, and q is an integer of from 0 to 2, or a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3, and wherein one of the single bonds of the ring so formed may optionally be replaced with a double bond, or a substituent of the formula —(CH$_2$)$_s$—X—(CH$_2$)$_t$—, where s and t are independently integers of from 0 to 3, and X is —O—, —NR'"—, —S—, —S(O)—, —S(O)$_2$—, or —S(O)$_2$NR'"— and the substituent R'" in —NR'"— and —S(O)$_2$NR'"— is selected from hydrogen or unsubstituted (C$_1$–C$_6$)alkyl;

R$^1$ is a member selected from the group consisting of substituted or unsubstituted (C$_5$–C$_{15}$)alkyl and (C$_{81}$–C$_{14}$)acyl group;

R$^2$ is a member selected from the group consisting of substituted or unsubstituted (C$_1$–C$_8$)alkyl;

each R$^3$ is independently a substituent selected from the group consisting of halogen, —OR$^b$, —OC(O)R$^b$, —NR$^b$R$^c$, —SR$^b$, —R$^b$, —CN, —NO$_2$, —CO$_2$R$^b$, —CONR$^b$R$^c$, —C(O)R$^b$, —OC(O)NR$^b$R$^c$, —NR$^c$C(O)R$^b$, —NR$^c$C(O)$_2$R$^b$, —NR$^b$—C(O)NR$^c$R$^d$, —NH—C(NH$_2$)=NH, —NR$^b$C(NH$_2$)=NH, —NH—C(NH$_2$)=NR$^b$, —S(O)R$_b$, —S(O)$_2$R$^b$, —S(O)$_2$NR$^b$R$^c$, —N$_3$, —CH(Ph)$_2$, perfluoro(C$_1$–C$_4$)alkoxy, and perfluoro(C$_1$–C$_4$)alkyl, and where R$^b$, R$^c$ and R$^d$ are independently selected from hydrogen, (C$_1$–C$_8$) alkyl and heteroalkyl, unsubstituted aryl and heteroaryl, unsubstituted aryl-(C$_1$–C$_4$)alkyl, and unsubstituted aryloxy-(C$_1$–C$_4$)alkyl;

Y is a member selected from the group consisting of substituted or unsubstituted (C$_2$–C$_8$)alkylene and substituted or unsubstituted (C$_2$–C$_8$)heteroalkylene;

Z is —NR$^4$R$^5$,

R$^4$ and R$^5$ are independently selected from the group consisting of hydrogen and (C$_1$–C$_8$)alkyl or taken together with the nitrogen atom to which each is attached to form a heterocyclyl with 5, 6, or 7-members or a heteroaryl; and, each of said substituted alkyl, heteroalkyl, alkylene or heteroalkylene of Y, R$^1$, R$^2$ is independently substituted with one or members independently selected from the group consisting of —OR$^e$, =O, =NR$^e$, =N—OR$^e$, —NR$^e$R$^f$, —SR$^e$, halogen, —SiR$^e$R$^f$R$^g$, —OC(O)R$^e$, —C(O)R$^e$, —CO$_2$R$^e$, —CONR$^e$R$^f$, —OC(O)NR$^e$R$^f$, —NR$^f$C(O)R$^e$, —NR$^e$—C(O)NR$^f$R$^g$, —NR$^f$C(O)$_2$R$^e$, —NH—C(NH$_2$)=NH, —NR$^e$C(NH$_2$)=NH, —NH—C(NH$_2$)=NR$^e$, —S(O)R$^e$, —S(O)$_2$R$^e$, —S(O)$_2$NR$^e$, —R$^f$, —CN and —NO$_2$ in a number ranging from zero to (2m'+1), wherein m' is the total number of carbon atoms in said alkyl, heteroalkyl, alkylene or heteroalkylene of said substituted alkyl, heteroalkyl, alkylene or heteroalkylene of Y, $R^1$, and $R^2$; and $R^e$, $R^f$ and $R^g$ each independently is hydrogen, unsubstituted $(C_1-C_8)$alkyl and heteroalkyl, unsubstituted aryl, aryl substituted with from 1 to 3 halogens, unsubstitated alkyl, alkoxy or thioalkoxy groups, or aryl-$(C_1-C_4)$alkyl groups; and optionally, when $R^e$ and $R^f$ are attached to the same nitrogen atom, $R^e$ and $R^f$ can be taken together with the nitrogen atom to form a heterocyclyl with 5, 6, or 7-members or a heteroaryl.

11. A composition in accordance with claim 10, wherein Ar is substituted phenyl.

12. A composition in accordance with claim 10, wherein Ar is substituted phenyl, and $R^1$ is a $(C_8-C_{14})$acyl group.

13. A composition in accordance with claim 10, wherein Ar is substituted phenyl, $R^1$ is a $(C_8-C_{14})$acyl group, and $R^2$ is unsubstituted $(C_1-C_4)$alkyl.

14. A composition in accordance with claim 10, wherein Ar is substituted phenyl, $R^1$ is a $(C_8-C_{14})$acyl group, $R^2$ is unsubstituted $(C_1-C_4)$alkyl, and Y is $(C_2-C_5)$alkylene.

15. A composition in accordance with claim 10, wherein Ar is substituted phenyl, $R^1$ is a $(C_8-C_{14})$acyl group, $R^2$ is unsubstituted $(C_1-C_4)$alkyl, Y is $(C_2-C_5)$alkylene, and Z is dimethylamino.

16. A composition in accordance with claim 10, wherein Ar is substituted phenyl, $R^1$ is a $(C_8-C_{14})$acyl group, $R^2$ is unsubstituted $(C_1-C_4)$alkyl, Y is $(C_2-C_5)$alkylene, Z is dimethylamino, and n is 0.

17. A composition in accordance with claim 10, wherein Ar is substituted phenyl, $R^1$ is a $(C_8-C_{14})$acyl group, $R^2$ is methyl, Y is ethylene, Z is dimethylamino, and n is 0.

18. A composition in accordance with claim 17, wherein said substituted phenyl is selected from the group consisting of 4-fluorophenyl, 4-methoxyphenyl, 4-chlorophenyl, 4-methylphenyl, and 4-bromophenyl.

19. A method of modulating CXCR3 function, said method comprising contacting a CXCR3 protein or truncated form thereof with a CXCR3-modulating amount of a compound having the formula:

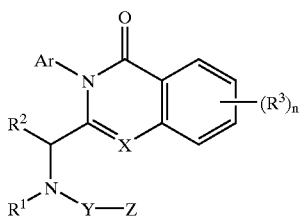

wherein,
the subscript n is an integer of from 0 to 4;
Ar is a member selected from the group consisting of substituted or unsubstituted aryl and substituted or unsubstituted heteroaryl, wherein each substituent of the substituted aryl or substituted heteroaryl is independently selected from the group consisting of halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro$(C_1-C_4)$alkoxy, and perfluoro$(C_1-C_4)$alkyl, wherein R', R"and R''' are independently selected from hydrogen, $(C_1-C_8)$alkyl and heteroalkyl, unsubstituted aryl and heteroaryl unsubstituted aryl-$(C_1-C_4)$alkyl, and unsubstituted aryloxy-$(C_1-C_4)$alkyl; and optionally further wherein two of the substituents on adjacent atoms of the aryl or heteroaryl ring may be replaced with a substituent of the formula -T-C(O)—(CH$_2$)$_q$-U- wherein T and U are independently —NH—, —O—, —CH$_2$— or a single bond, and q is an integer of from 0 to 2, or a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3, and wherein one of the single bonds of the ring so formed may optionally be replaced with a double bond, or a substituent of the formula —(CH$_2$)$_s$—X—(CH$_2$)$_t$—, where s and t are independently integers of from 0 to 3, and X is —O—, —NR'''—, —S—, —S(O)—, —S(O)$_2$—, or —S(O)$_2$NR'''— and the substituent R''' in —NR'''— and —S(O)$_2$NR'''— is selected from hydrogen or unsubstituted $(C_1-C_6)$alkyl;

$R^1$ is a member selected from the group consisting of substituted or unsubstituted $(C_5-C_{15})$alkyl and $(C_8-C_{14})$acyl group;

$R^2$ is a member selected from the group consisting of substituted or unsubstituted $(C_1-C_8)$alkyl;

each $R^3$ is independently a substituent selected from the group consisting of halogen, —OR$^b$, —OC(O)R$^b$, —NR$^b$R$^b$, —SR$^b$, —R$^b$, —CN, —NO$_2$, —CO$_2$R$^b$, —CONR$^b$R$^c$, —C(O)R$^b$, —OC(O)NR$^b$R$^c$, —NR$^c$C(O)R$^b$, —NR$^c$C(O)$_2$R$^b$, —NR$^b$—C(O)NR$^c$R$^d$, —NH—C(NH$_2$)=NH, —NR$^b$C(NH$_2$)=NH, —NH—C(NH$_2$)=NR$^b$, —S(O)R$_b$, —S(O)$_2$R$^b$, —S(O)$_2$NR$^b$R$^c$, —N$_3$, —CH(Ph)$_2$, perfluoro$(C_1-C_4)$alkoxy, and perfluoro$(C_1-C_4)$alkyl, and where R$^b$, R$^c$ and R$^d$ are independently selected from hydrogen, $(C_1-C_8)$ alkyl and heteroalkyl, unsubstituted aryl and heteroaryl, unsubstituted aryl-$(C_1-C_4)$alkyl, and unsubstituted aryloxy-$(C_1-C_4)$alkyl;

Y is a member selected from the group consisting of substituted or unsubstituted $(C_2-C_8)$alkylene and substituted or unsubstituted $(C_2-C_8)$heteroalkylene;

Z is —NR$^4$R$^5$;

wherein R$^4$ and R$^5$ are independently selected from the group consisting of hydrogen and $(C_1-C_8)$ alkyl or taken together with the nitrogen atom to which each is attached to form a heterocyclyl with 5, 6, or 7-members or a heteroaryl; and, wherein each of said substituted alkyl, heteroalkly, alkylene or heteroalkylene of Y, $R^1$, $R^2$ is independently substituted with one or members independently selected from the group consisting of —OR$^e$, =O, =NR$^e$, =N—OR$^e$, —NR$^e$R$^f$, —SR$^e$, halogen, —SiR$^e$R$^f$R$^g$, —OC(O)R$^e$, —C(O)R$^e$, —CO$_2$R$^e$, —CONR$^e$R$^f$, —OC(O)NR$^e$R$^f$, —NR$^f$C(O)R$^e$, —NR$^e$—C(O)NR$^f$R$^g$, —NR$^f$C(O)$_2$R$^e$, —NH—C(NH$_2$)=NH, —NR$^e$C(NH$_2$)=NH, —NH—C(NH$_2$)=NR$^e$, —S(O)R$^e$, —S(O)$_2$R$^e$, —S(O)$_2$NR$^e$, —R$^f$, —CN and —NO$_2$ in a number ranging from zero to (2m'+1), wherein m' is the total number of carbon atoms in said alkyl, heteroalkyl, alkylene or heteroalkylene of said substituted alkyl, heteroalkyl, alkylene or heteroalkylene of Y, $R^1$, and $R^2$; and R$^e$, R$^f$ and R$^g$ each independently is hydrogen, unsubstituted $(C_1-C_8)$alkyl and heteroalkyl, unsubstituted aryl, aryl substituted with from 1 to 3 halogens, unsubstituted alkyl, alkoxy or thioalkoxy groups, or aryl-$(C_1-C_4)$alkyl groups; and optionally, when $R^e$ and $R^f$ are attached to the same nitrogen atom, $R^e$ and $R^f$ can be taken together with the nitrogen atom to form a heterocyclyl with 5, 6, or 7-members or a heteroaryl.

20. A compound in accordance with claim 1, wherein:
$R^4$ and $R^5$ are optionally taken together with the nitrogen atom to which each is attached to form a pyrrolidinyl or piperdinyl; and
$R^e$ and $R^f$ can be taken together with the nitrogen atom to form a pyrrolidinyl or morpholinyl.

21. A composition in accordance with claim 10, wherein:
$R^4$ and $R^5$ are optionally taken together with the nitrogen atom to which each is attached to form a pyrrolidinyl or piperdinyl; and
$R^e$ and $R^f$ can be taken together with the nitrogen atom to form a pyrrolidinyl or morpholinyl.

22. The method of claim 19, wherein:
$R^4$ and $R^5$ are optionally taken together with the nitrogen atom to which each is attached to form a pyrrolidinyl or piperdinyl; and
$R^e$ and $R^f$ can be taken together with the nitrogen atom to form a pyrrolidinyl or morpholinyl.

* * * * *

UNITED STATES PATENT AND TRADEMARK OFFICE
CERTIFICATE OF CORRECTION

PATENT NO. : 6,992,084 B2
APPLICATION NO. : 10/279353
DATED : January 31, 2006
INVENTOR(S) : Schall et al.

It is certified that error appears in the above-identified patent and that said Letters Patent is hereby corrected as shown below:

In the abstract, line 3; claim 1, lines 57-67; claim 10, lines 47-59; and claim 19, lines 44-54, the chemical structure, for each occurrence should be:

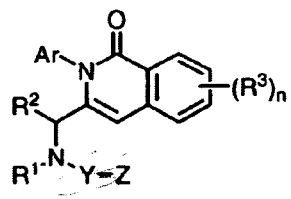

In claim 10, column 40, line 30, "$(C_{81}-C_{14})$acyl" should be deleted and substituted --$(C_8-C_{14})$acyl.--

Signed and Sealed this

Fourteenth Day of November, 2006

JON W. DUDAS
*Director of the United States Patent and Trademark Office*